(12) United States Patent
Almodovar

(10) Patent No.: US 11,666,326 B2
(45) Date of Patent: Jun. 6, 2023

(54) THREADING DEVICES AND METHODS OF MANUFACTURE AND USE THEREOF

(71) Applicant: Ergosurgical Group Corp., Arlington, MA (US)

(72) Inventor: Luis Jose Almodovar, San Juan, PR (US)

(73) Assignee: Ergosurgical Group Corp., Arlington, MA (US)

( * ) Notice: Subject to any disclaimer, the term of this patent is extended or adjusted under 35 U.S.C. 154(b) by 503 days.

(21) Appl. No.: 16/920,619

(22) Filed: Jul. 3, 2020

(65) Prior Publication Data
US 2021/0022729 A1    Jan. 28, 2021

Related U.S. Application Data

(60) Provisional application No. 62/870,407, filed on Jul. 3, 2019.

(51) Int. Cl.
*A61B 17/06* (2006.01)
*A61B 17/04* (2006.01)
*A61B 17/00* (2006.01)

(52) U.S. Cl.
CPC .... *A61B 17/06004* (2013.01); *A61B 17/0469* (2013.01); *A61B 2017/00243* (2013.01); *A61B 2017/00867* (2013.01); *A61B 2017/0477* (2013.01)

(58) Field of Classification Search
CPC ............ A61B 17/0625; A61B 17/0466; A61B 17/0482; A61B 17/0485; A61B 2017/0411; A61B 2017/0472; A61B 2017/0477; A61B 2017/0488; A61B 2017/049
See application file for complete search history.

(56) References Cited

U.S. PATENT DOCUMENTS

| | | | | |
|---|---|---|---|---|
| 5,810,848 | A | * | 9/1998 | Hayhurst ............... A61B 17/04 606/232 |
| 2003/0216613 | A1 | | 11/2003 | Suzuki |
| 2005/0251159 | A1 | | 11/2005 | Ewers |
| 2013/0096613 | A1 | | 4/2013 | Hart |
| 2014/0058417 | A1 | | 2/2014 | Levy |
| 2016/0015376 | A1 | | 1/2016 | Riina |
| 2020/0129173 | A1 | * | 4/2020 | Hiernaux ........... A61B 17/0482 |

FOREIGN PATENT DOCUMENTS

| | | |
|---|---|---|
| WO | WO9807374 | 2/1998 |
| WO | WO2005034729 | 4/2005 |

OTHER PUBLICATIONS

International Search Report and Written Opinion dated Sep. 23, 2020 in related International Application No. PCT/US2020/040831 filed Jul. 3, 2020 (11 pages).

* cited by examiner

*Primary Examiner* — Katherine M Shi
*Assistant Examiner* — Mohammed S Adam
(74) *Attorney, Agent, or Firm* — Dentons US LLP

(57) ABSTRACT

This disclosure enables various threading devices (e.g., suturing devices) that can sequentially send a plurality of carriers (e.g., needle caps, sleeves) to an object (e.g., animate, inanimate, human tissue, organ tissue, heart tissue) or sequentially receive a plurality of carriers (e.g., needle caps, sleeves) from an object (e.g., animate, inanimate, human tissue, organ tissue, heart tissue). For example, some threading devices can sequentially send some carriers in a relatively rapid succession or some threading devices can sequentially receive some carriers in a relatively rapid succession.

33 Claims, 27 Drawing Sheets

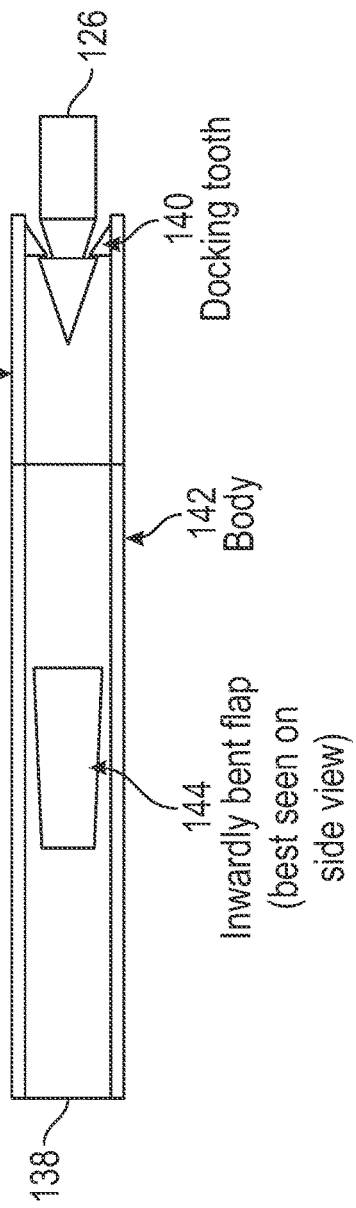
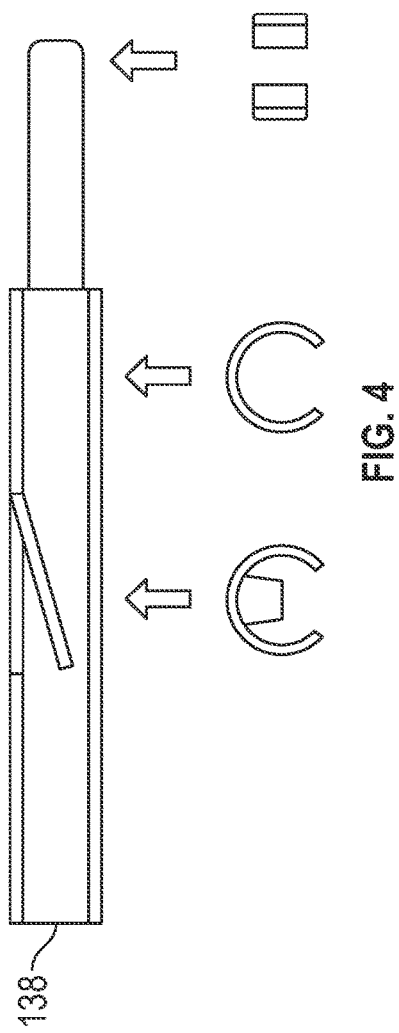
FIG. 4

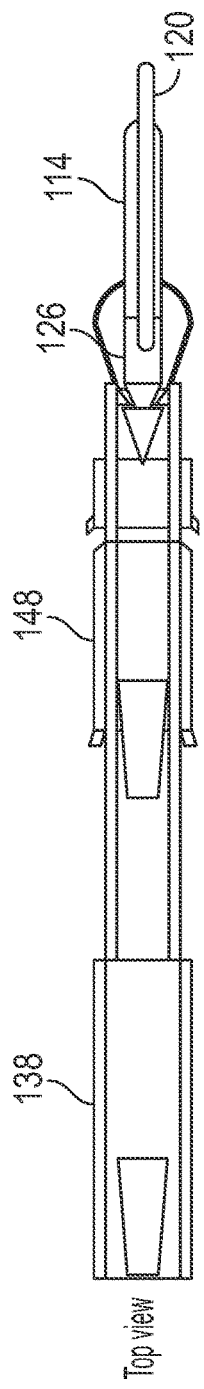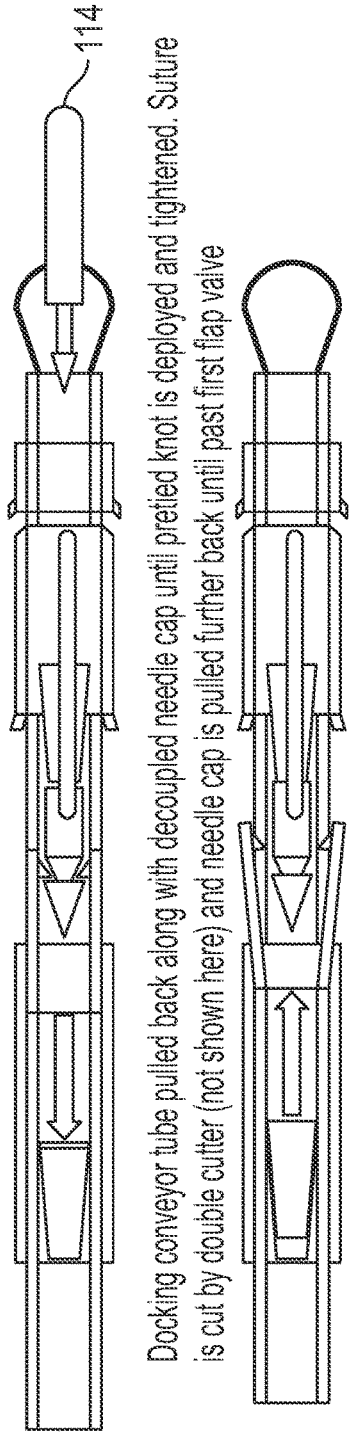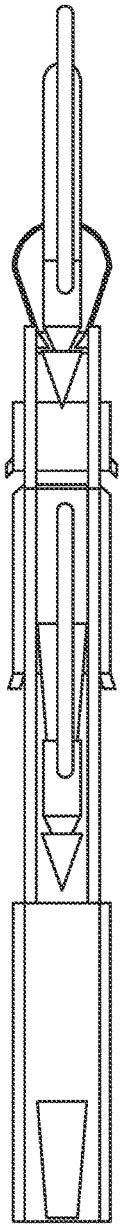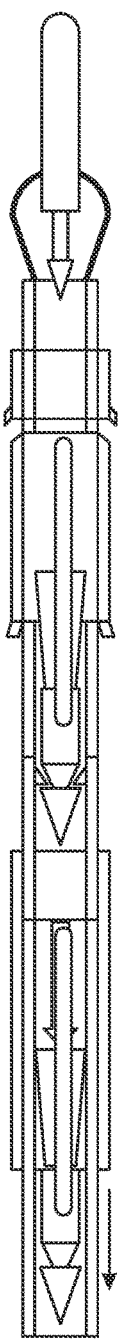
FIG. 10

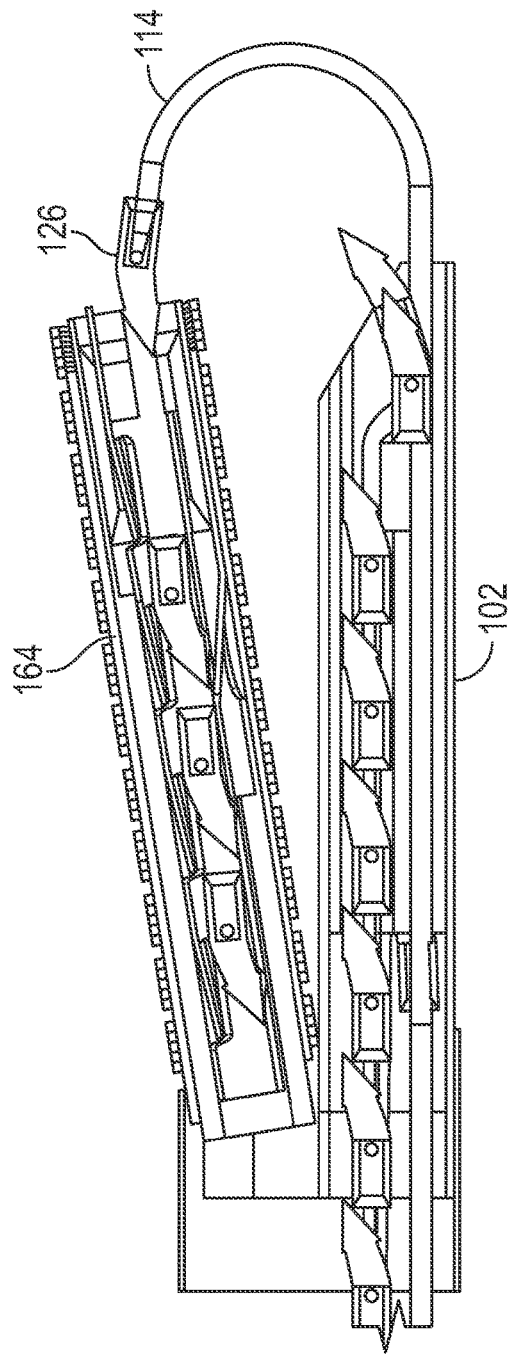

- Catheter based delivery system for suturing (or other type of threading or stitching of animate or inanimate material).
- Bottom delivery section has series of curved needles (red) with attached sutures that are pushed by a Nitinol (or another shape memory material) Pusher around a curved path through tissue (or another animate or inanimate material).
- Top section is the receiving end which will capture the Needle and push into the tube going thru the half knot that is on the OD of the tube.
- The half knots will slide off the tube and the suture (or another thread type) will be pulled tight to secure the implant (animate or inanimate) and then the suture will be cut and the needle will be retained.
- The process is then repeated 10 - 12 times (although more or less is possible).

FIG. 13

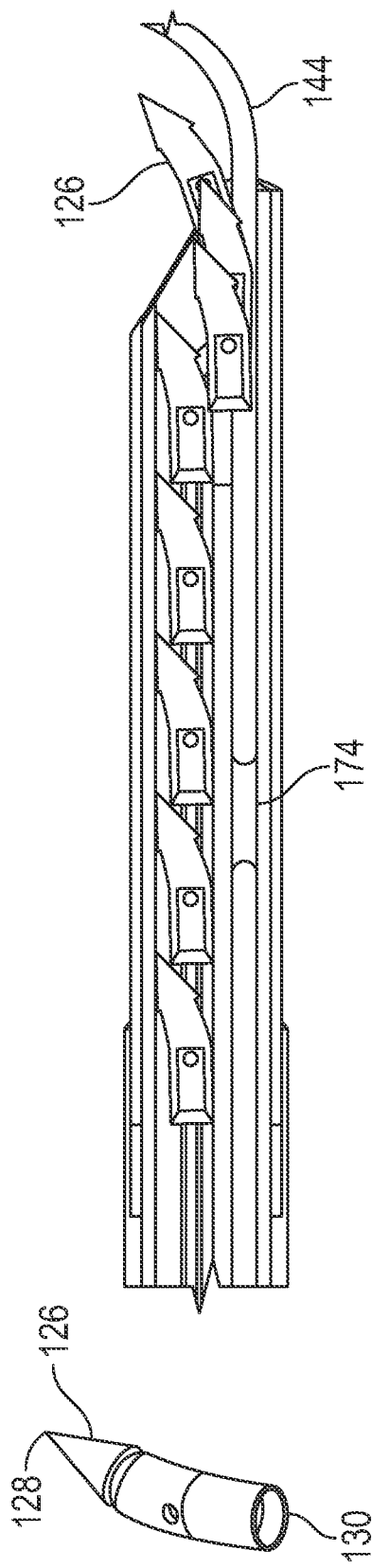

NEEDLE CONFIGURATION/SHAPE MEMORY MATERIAL/NITINOL

- Needle feed system and pre-bent shape is shown
  - Angled tip and exit window channeling geometry
  - Reliably feeding needles and capturing in a traditional laparoscopic type feed system with a curved nitinol pusher and curved needle.
  - Transitioning sharp asymmetrical design of needle through a catheter.
- The Nitinol pusher as the needle.
  - This simplifies the feed system and reduces the possibility of jamming. As well as the need to constrain from rotation and improves the entry angle into tissue (or another animate or inanimate material).
- This part can become a Sleeve-Suture that attaches to the Nitinol Needle.

FIG. 14

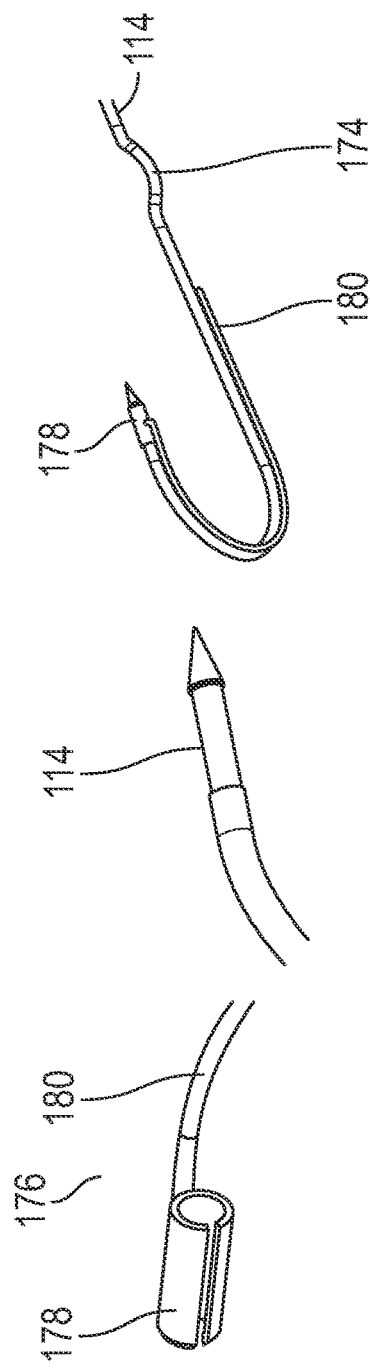

SHAPE MEMORY MATERIAL/NITINOL NEEDLE CONCEPT

- Nitinol (or another shape memory material) Needle reliably hits target and is captured after passing through the tissue (or another animate or inanimate material).
- Pushing force is not excessive and can be sufficient or controlled.
- Geometry of Sleeve- Suture / Nitinol Needle for capture and recapture has a small size sufficient for its use.
- Needle can be structured to avoid (1) bending or rotating out of plane (polygonal, square, rectangle, triangle, teardrop, with corner, with longitudinal bend), (2) needle carrying tissue into the receiver (tissue filter on receiver), (3) not be able to release and later reengage the Sleeve-Suture.
- Needle can be a pre-bent nitinol needle shape that can pass through tissue and hit target 100%.

FIG. 15

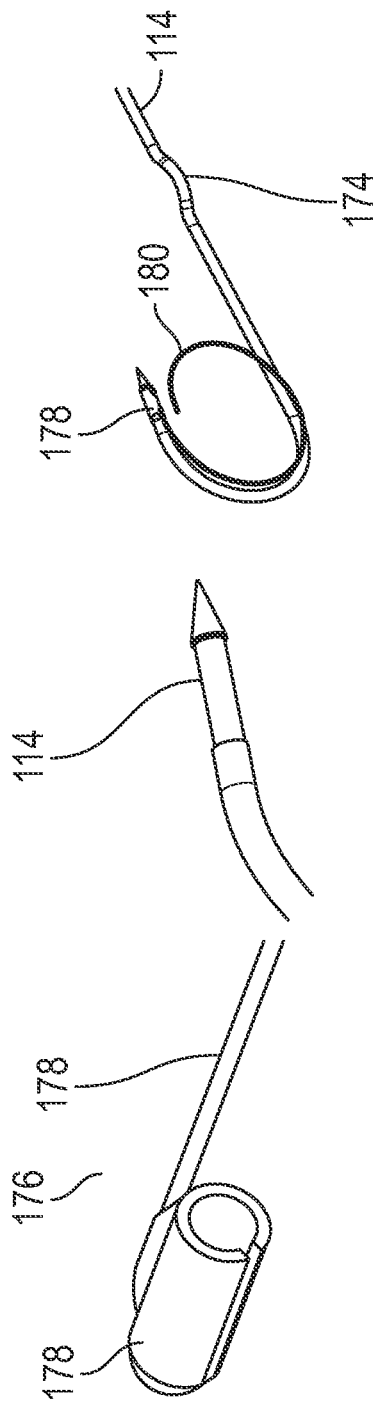

SHAPE MEMORY MATERIAL/NITINOL NEEDLE CONCEPT

- In some cases, overall diameter can be as close to the diameter of a 2-0 Needle (.53mm). In some cases, there is a Ø1.0 & .63mm Nitinol structure. Note that other dimensions can be greater or lesser.
- Able to pass Sleeve-Suture thru the tissue and then capture in the Receiver Tube, retract the Nitinol Needle back thru the tissue and then outside of the tissue go and retrieve the Sleeve-Suture and then back thru tissue is shown.
- Nitinol needle shape development (e.g. different diameters .5mm, .63mm, 1.00mm)
- Nitinol needle with ground detail for sharp and relief for Sleeve-Suture
- Distal end – needle Block for anti-rotation

FIG. 16

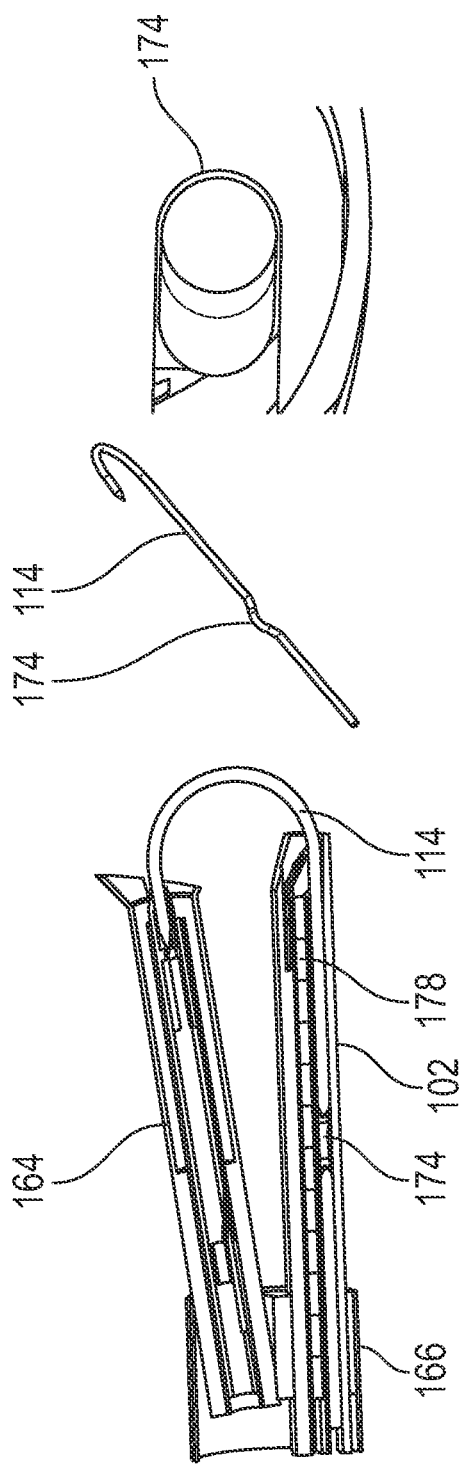

SHAPE MEMORY MATERIAL/NITINOL NEEDLE ANTI-ROTATION

- Constrains the Nitinol pusher from rotation during deployment.
- Curved section will ride in anti-rotation slot.
- Needle can be configured to avoid twisting while going thru the tissue through bending.
- Other ways to reduce anti-rotation can include introducing at least one corner (e.g. polygon, teardrop, square, rectangle, triangular cross-section).

FIG. 17

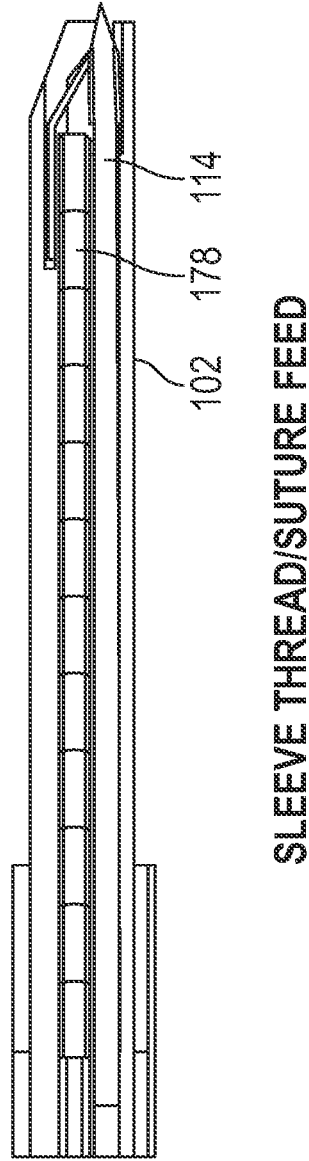

SLEEVE THREAD/SUTURE FEED

- Transition from catheter to rigid (or flexible) section can be manufactured.
- Trans-septal approach can allow for flexible (or rigid) pushing elements.
- In the rigid section there can be a laparoscopic feed system.
- With the straight section sleeve, the feed section may be less likely to jam
- Pick up of the sleeve onto the Nitinol is possible.
- Retention features on the Sleeve have simple geometry due to the scale and have multiple drop off and pick up to achieve design
- Prevents snagging of the suture on other components or tissue.
- Minimizes jamming, suture entanglement, failure to pick up and release.

FIG. 18

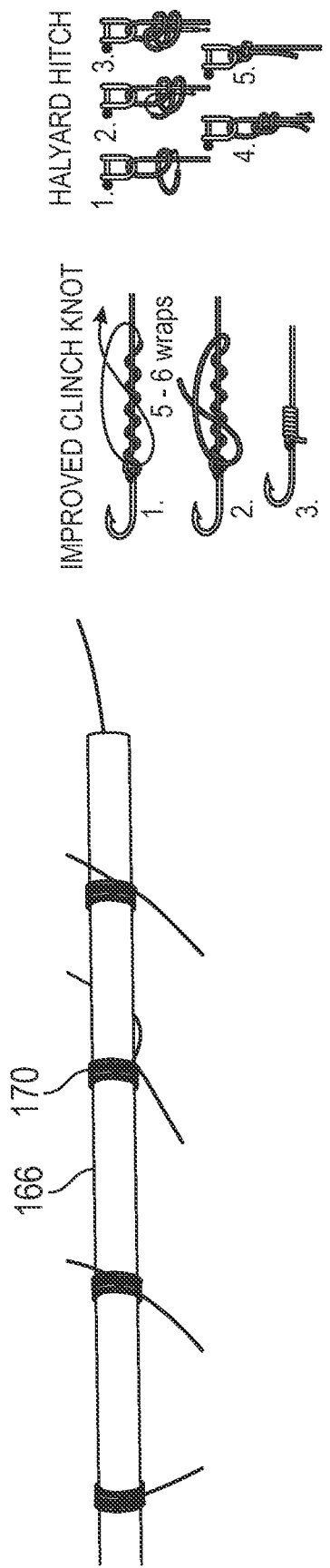

- The knots are structured to get the needle thru the center and then pulling the suture to secure.
- Custom knot can be used to secure the half knot on the Receiver tube.
  - Having the half knot hold its' shape prior and during deployment can be done with or without an addition half hitch.
- Reliability of knot holding shape and consistently pulling tight and locking every time.
- Getting the knot off the tube and forming correctly every time can be done.
- A deployment system can be used to manage the knots.
- Some knots that can be used includes the improved clinch knot and the halyard knot, especially when an additional half hitch was added. For example, only one half knot can come off at a time or a plurality of sutures (e.g. 2-20) can be handled without becoming entangled

FIG. 19

- With both the Improved Clinch Knot and the Halyard Knot, the knot can tighten around a foam piece and remain secure.
- The knot can be consistently and repeatably formed.
- The Improved Clinch Knot and the Halyard Knot have an addition half hitch to secure to the deployment tube.

- Deploying the pre-tied portions is shown.
- Axial space can be present for 12 knots (or less or more) and ensure deployment
- The knot can reliably can hold its shape and consistently pulling tight and locking every time.

Knot Alternatives

- One or multiple Suture Sleeve (tubular, closed or open perimeter or circumference) as a dynamic capture detail for the suture.
  - Grab the suture and pull it thru a Sleeve-Suture.
  - Multiple types of features on suture sleeve to provide primary and secondary attachment
  - Suture management during transfer and output

FIG. 22

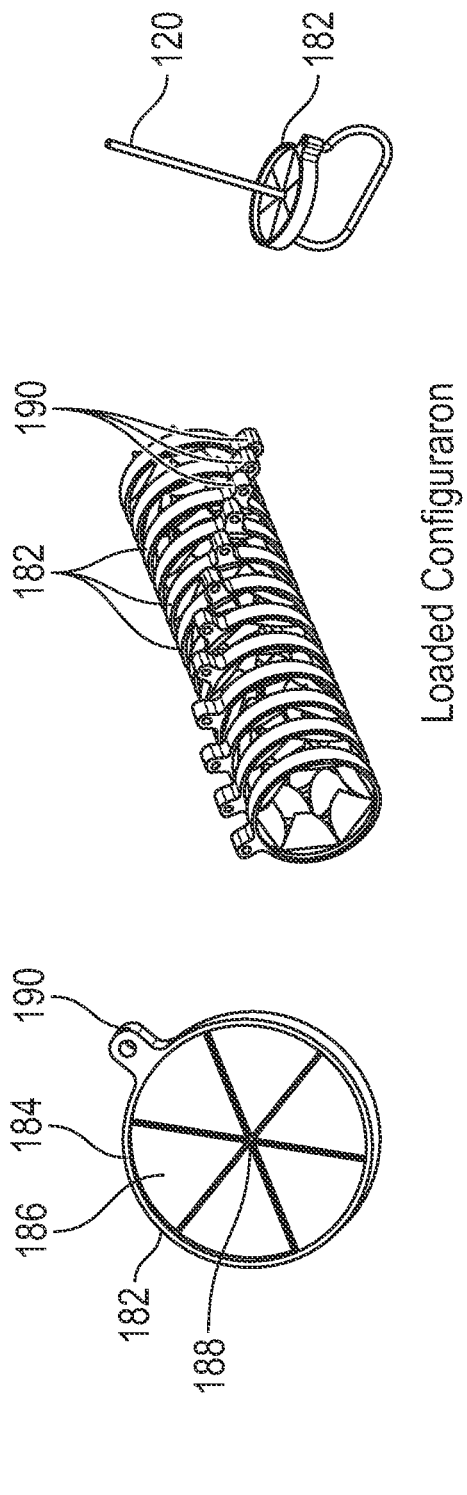

Loaded Configuraron

CLEAT
- Cleat to secure the suture.
- Micro Molding can be used to achieve this approach. The diameter can be Ø2.9 mm (or less or more).
- Material selection can include polymer, plastic, metal, alloy, shape memory, rubber.
- Securement during pulsatile cyclic forces
- Non-circular shapes are possible (e.g. oval, square, rectangle, pentagon, octagon, triangle)
- More than six or less than six leaves are possible
- Leaves or body can be symmetrical or asymmetrical
- Difference between loaded diameter and suture (or thread) diameter
- Can be sterilized or work on beating heart (or another organ whether moving or not)
- Can have sleeve-sutures at size or pull or holding forces

FIG. 23

SUTURE MANAGEMENT

- The distance pulled to tighten the suture prior to cutting is consistent for all shots.
- Management of the sutures to minimize or avoid tangling to each other, the device or anatomy.
- This will be the case regardless of use of the knots, the Suture Sleeve or Cleats.

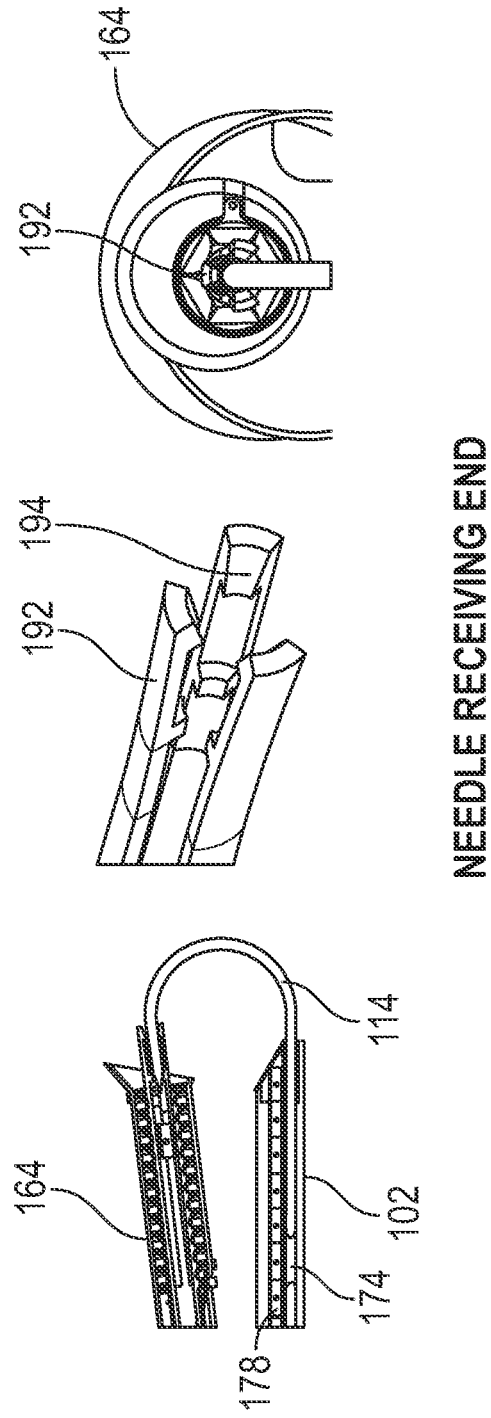

NEEDLE RECEIVING END

- The deployment (Sleeve/needle) end of the device operates with the Receiving end.
- Docking Conveyor Tube can be Nitinol (or another shape memory material or polymer, plastic, metal, alloy, rubber) and will be in a normally open position. When pulled back into the device, the Docking ConveyorTube will capture the Sleeve-Suture and be pulled into the device to tension the suture (or another thread) and cut.
- Releasing and storing proximally the spent Sleeve-Suture depends upon how the deployment of the cleat end up.
- Docking Conveyer Tube retrieves Sleeve-Suture off of Nitinol (or another shape memory material or non-shape memory material or polymer, plastic, metal, alloy, rubber) or Needle and releases and stores spent Sleeves at scale repeatably while working within confined space and minimizing tissue entrapment

FIG. 25

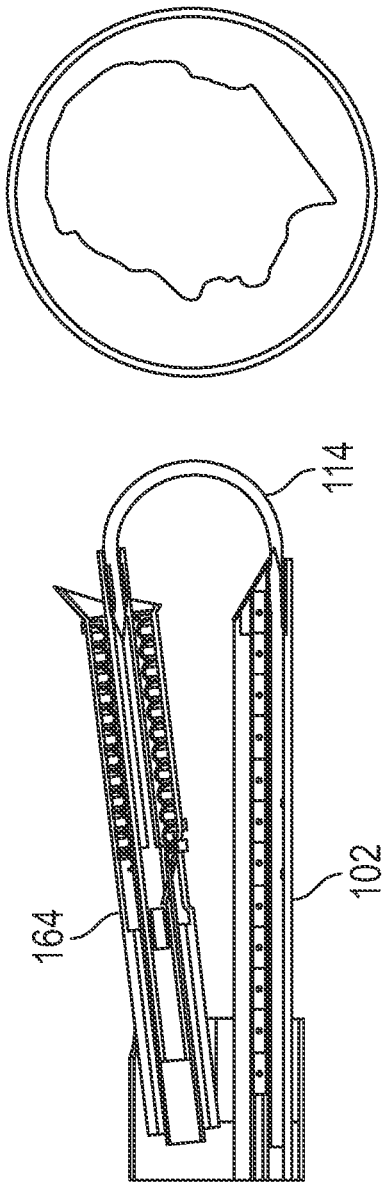

SCALE OF DEVICE

- 24 Fr OD (but this can vary whether smaller or larger)
  - Device has been modeled with .010" tubing in standard diameters (but this can vary whether smaller or larger).
- Knots or cleats occupying a percentage of OD (e.g. at least 5, 10, 15, 20, 25, 30, 35, 40, 45, 50, 55, 60, 65, 70, 75, 80, 80, 90, 95 percent)
- Include a system for managing deployment of cleats/knots or the cutting of the suture after securing.
- Knots - the retention funnel feature can be eliminated.
- A no-funnel design can work.

FIG. 26

Catheter

- Transseptal approach has a purpose built catheter.
- The device has several push pull actuations with specific strokes
- The catheter can be elongated given the femoral access and transseptal approach.
  - Compression characteristics under high deployment loads are accomodated by the design.
  - Transitions and accommodating rigid components actuated around the transseptal puncture.
- Length of a rigid (or flexible) member can be 20-30 cm (or lesser or greater).
- Catheter can be steerable.

FIG. 27

US 11,666,326 B2

THREADING DEVICES AND METHODS OF MANUFACTURE AND USE THEREOF

CROSS-REFERENCE TO RELATED PATENT APPLICATIONS

This patent application claims a benefit of U.S. Provisional Patent Application 62/870,407 filed 3 Jul. 2019; which is incorporated by reference herein for all purposes.

TECHNICAL FIELD

This disclosure relates to threading.

BACKGROUND

There are some situations where surgical suturing is desired to be performed on a sequential basis (e.g., heart tissue). However, such technologies are not known to exist. Accordingly, this disclosure enables such technologies.

SUMMARY

Broadly, this disclosure enables various threading devices (e.g., suturing devices) that can sequentially send a plurality of carriers (e.g., needle caps, sleeves) to an object (e.g., animate, inanimate, human tissue, organ tissue, heart tissue) or sequentially receive a plurality of carriers (e.g., needle caps, sleeves) from an object (e.g., animate, inanimate, human tissue, organ tissue, heart tissue). For example, some threading devices can sequentially send some carriers in a relatively rapid succession or some threading devices can sequentially receive some carriers in a relatively rapid succession.

An embodiment can include a device comprising: a tube having a proximal end portion and a distal end portion, wherein the tube includes a first section and a second section, wherein each of the first section and the second section extends from the proximal end portion towards the distal end portion, wherein the first section is adjacent to the second section; a rod extending within the first section; a plurality of carriers extending within the second section; a plurality of threads extending from the carriers, wherein each of the carriers is movable from the second section to the first section when each of the carriers is positioned at the proximal end portion such that the rod (a) engages that respective carrier from which that respective thread extends, (b) enters an object from the proximal end portion of the first cavity at a first point while carrying that respective carrier from which that respective thread extends, and (c) exits the object at a second point while carrying that respective carrier from which that respective thread extends, wherein the first point is spaced apart from the second point, wherein the rod arcuately travels between the first point and the second point, wherein each of the carriers is separated from the rod after exiting the object.

DESCRIPTION OF DRAWINGS

FIG. 4 illustrates an embodiment of a threading device having a tube for sequentially receiving a plurality of carriers according to this disclosure.

FIG. 10 illustrates an embodiment of a threading device sequentially receiving a plurality of carriers from a rod according to this disclosure.

FIG. 13 illustrates an embodiment of a threading device having a tube that outputs a plurality of carriers along an arcuate path and a tube that receives the carriers from the arcuate path according to this disclosure.

FIG. 14 illustrates an embodiment of a threading device containing a plurality of carriers according to this disclosure.

FIG. 15 illustrates an embodiment of a rod engaging a carrier with a thread where the thread follows the rod according to this disclosure.

FIG. 16 illustrates an embodiment of a rod engaging a carrier with a thread where the thread does not follow the rod according to this disclosure.

FIG. 17 illustrates an embodiment of a threading device hosting a rod with a bend according to this disclosure.

FIG. 18 illustrates an embodiment of a threading device sequentially hosting a plurality of carriers according to this disclosure.

FIG. 19 illustrates an embodiment of a pre-tied knot extending about a rigid tube according to this disclosure.

FIG. 22 illustrates an embodiment of a plurality of knot alternatives according to this disclosure.

FIG. 23 illustrates an embodiment of a cleat having a plurality of leaves that resiliently or elastically flex from a default configuration into a non-default configuration while being consecutively offset with each other according to this disclosure.

FIG. 25 illustrates an embodiment of a threading device having a tube with a plurality of fingers for grasping a carrier according to this disclosure.

FIG. 26 illustrates an embodiment of a threading device scaled relative to a coin according to this disclosure.

FIG. 27 illustrates an embodiment of a catheter according to this disclosure.

DETAILED DESCRIPTION

Figure 1:
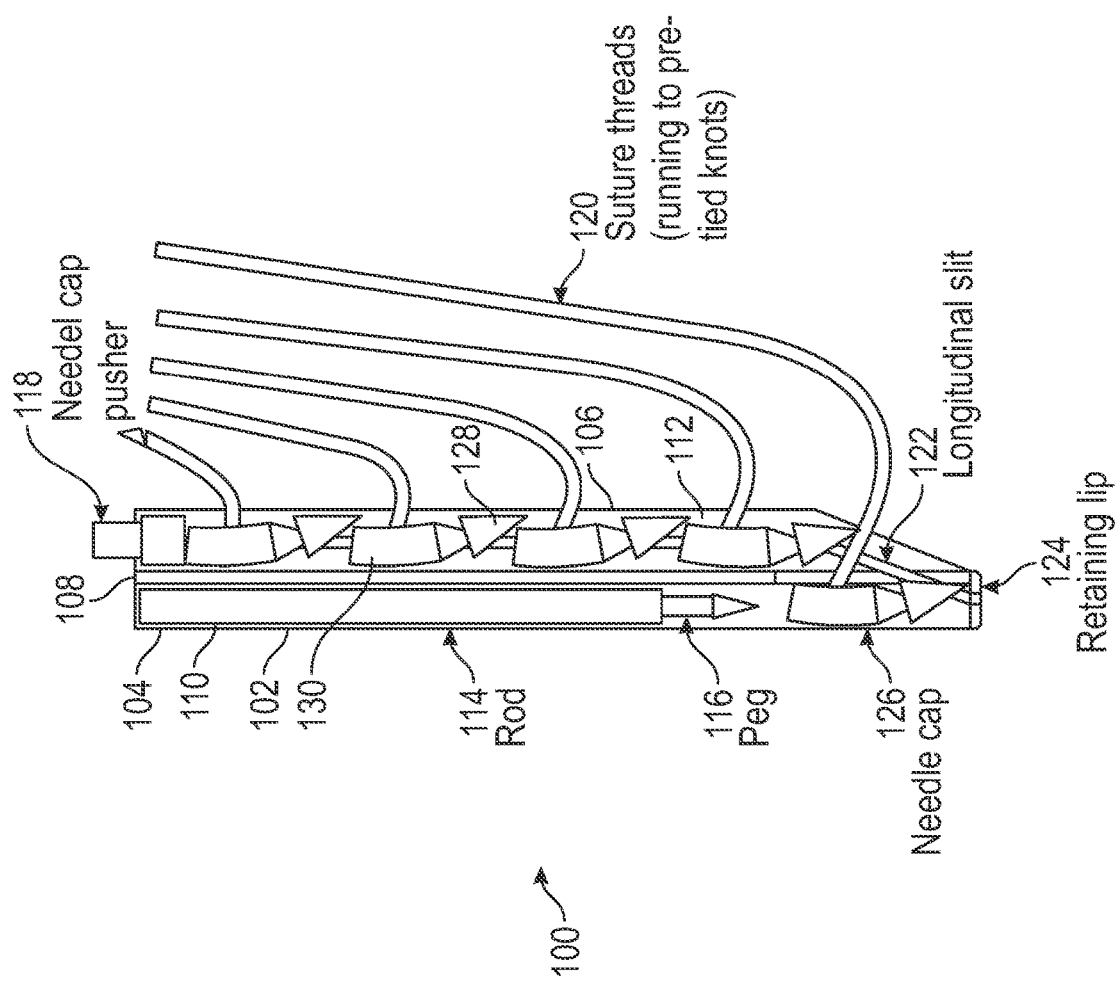
FIG. 1 illustrates an embodiment of a threading device for sequentially output a plurality of carriers according to this disclosure.

Broadly, this disclosure enables various threading devices (e.g., suturing devices) that can sequentially send a plurality of carriers (e.g., needle caps, sleeves) to an object (e.g., animate, inanimate, human tissue, organ tissue, heart tissue) or sequentially receive a plurality of carriers (e.g., needle caps, sleeves) from an object (e.g., animate, inanimate, human tissue, organ tissue, heart tissue). For example, some threading devices can sequentially send some carriers in a relatively rapid succession or some threading devices can sequentially receive some carriers in a relatively rapid succession.

In some embodiments, there is a desire to increase versatility/ease of use of various threading devices (e.g., suturing medical instruments), while decreasing procedure-related time, complexity, and risk. For example, there is a desire to configure some threading devices (e.g., suturing medical instruments) that have various multi-output capabilities with automatic reloading of subsequent needle or analogous structure to avoid muzzle-loading each time a thread (e.g., suture) needs to be placed. Likewise, there is a desire to configure some threading devices (e.g., suturing medical instruments) to enable material (e.g., tissue) anchoring as well as material (e.g., tissue) approximation capabilities (e.g., ability to grasp and release needle or analogous suture-passing structure as to return the needle or the analogous suture-passing structure to an initial firing position so the needle or the analogous suture-passing structure can pierce a material (e.g., tissue) a second time at a different location). Similarly, there is a desire to configure some threading devices (e.g., suturing medical instruments) to enable threading (e.g., suturing), while minimizing or avoiding securing clips and maximizing pre-tied knots. Furthermore, there is a desire to configure some threading devices (e.g., suturing medical instruments) to be capable of securing a knot followed by simultaneous cutting of both thread limbs. Additionally, there is a desire to configure some threading devices (e.g., suturing medical instruments) to enable an automatic removal of a used-up needle and a thread remnant after each material (e.g., tissue) anchoring or material (e.g., tissue) approximation cycle. Also, there is a desire to configure some threading devices (e.g., suturing medical instruments) to have a control unit designed to coordinate device component actuation as to minimize operational steps. In addition, there is a desire to configure some threading devices (e.g., suturing medical instruments) to be a partially or fully integrated threading (e.g., suturing) system capable of carrying out some, many, most, or all tasks involved in threading (e.g., suturing) and not just driving needle through material (e.g., tissue). Accordingly, the threading devices, as disclosed herein, enable these possibilities.

In some embodiments, some of these threading devices create some time efficiencies achieved with staples but with a very wide versatility and tried-and-true reliability of threads (e.g., sutures), all in a multi-output, semi-automated or fully-automated platform. Some of these threading devices can be used for medical purposes (e.g., suturing). For example, some of these threading devices can be used in transcatheter suturing, transcatheter intracardiac (or another body organ) suturing, and other flexible platform applications (e.g., endoscopic suturing, colonoscopic suturing). For example, rigid shaft embodiments, as commonly used for laparoscopic, video-assisted thoracoscopic surgery (VATS) and robotic surgery can be used to fundamentally transform suture-based tissue approximation/anchoring from a laborious task to a swift semi-automated or fully-automated endeavor. For example, some of these threading devices can be used for an open surgery, a minimally invasive surgery, a laparoscopic surgery, or an end effector robotic surgery. As such, the some of these threading devices can be used for manual surgery or automated surgery. Some examples of surgeries where some of these threading devices can be employed include laparoscopic surgery, robotic surgery, video-assisted or unassisted thoracoscopic surgery, arthroscopic surgery, natural orifice surgery, endoscopic surgery, gynecologic surgery, cardiac surgery, colorectal surgery, pulmonary surgery, gastric bypass surgery, hysterectomy surgery, dental surgery, urological surgery, brain surgery, or bariatric surgery, or among many others in human (e.g., between newborn until 120 years old, male, female) or animal (e.g., mammal, birds, fish, land animals) applications.

Note that some of these threading devices can be employed in medical or non-medical settings, whether on an object is animate or inanimate. For example, the object, when animate, can include a tissue, an organ, a body part, whether of human or animal, or others. For example, the tissue can be a muscle tissue, a bone tissue, a nerve tissue, an organ tissue, or others. For example, the object, when inanimate, can include a medical device, a prosthesis, an implantable, a machine, a surgical instrument, or others. For example, some of the non-medical setting can include garment making, fabric stitching, knot applications, sowing, shoe making, or others.

Figure 2:
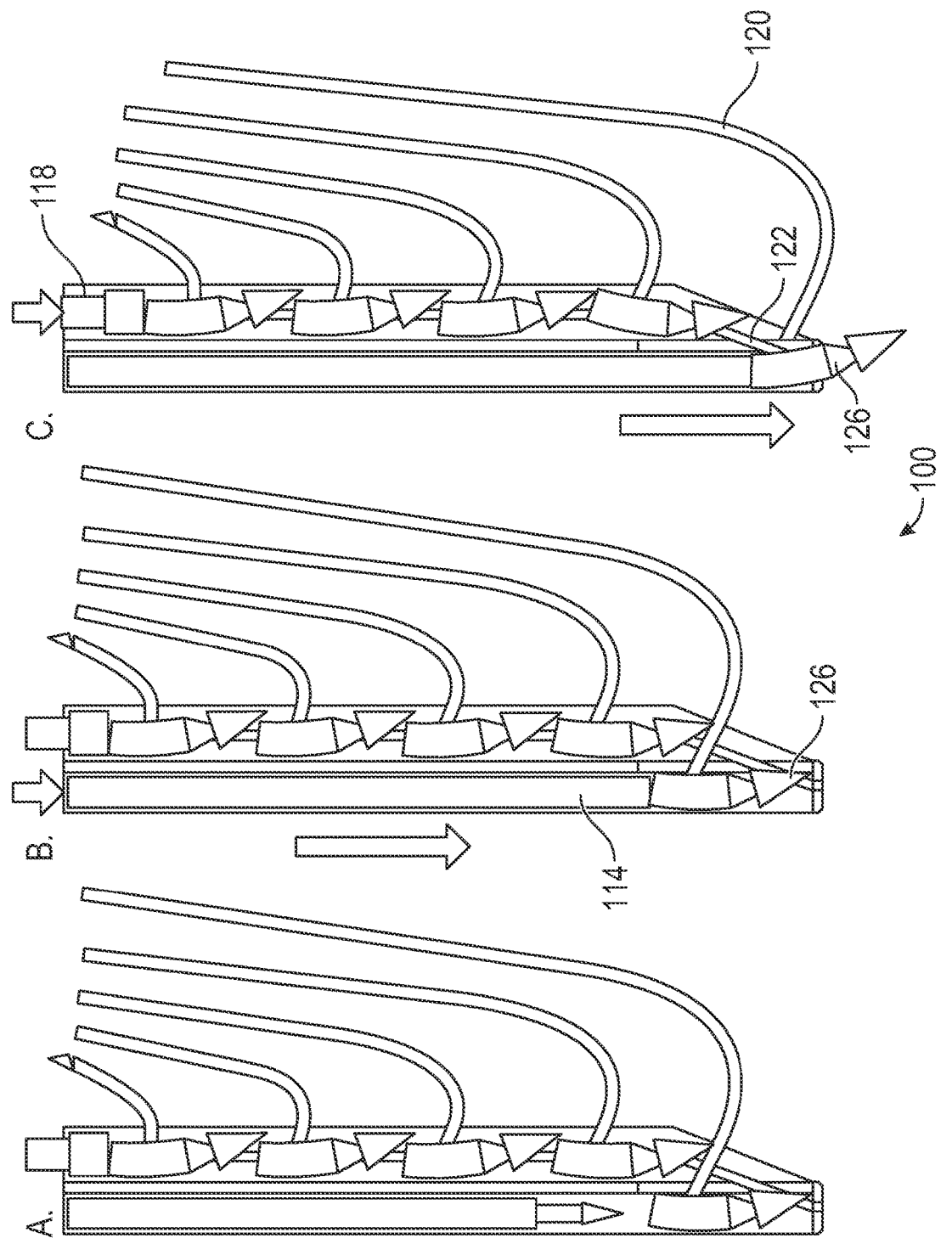
FIG. 2 illustrates an embodiment of a process for a threading device to sequentially output a plurality of carriers according to this disclosure.
Figure 3:
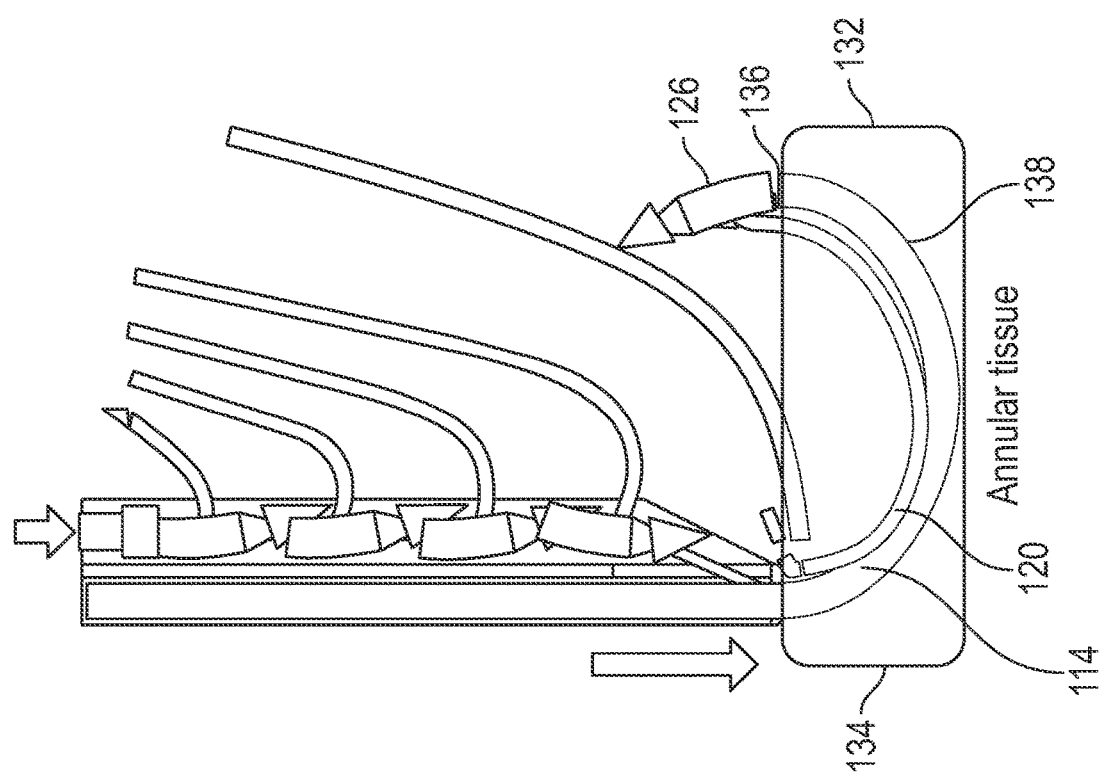
FIG. 3 illustrates an embodiment of a threading device sequentially sending a plurality of carriers into an object and out of the object according to this disclosure.

FIG. 1 illustrates an embodiment of a threading device for sequentially output a plurality of carriers according to this disclosure. FIG. 2 illustrates an embodiment of a process for a threading device to sequentially output a plurality of carriers according to this disclosure. FIG. 3 illustrates an embodiment of a threading device sequentially sending a plurality of carriers into an object and out of the object according to this disclosure. In particular, a device 100 includes a tube 102 having a proximal end portion and a distal end portion, where the tube 102 includes a first section 104 having a first cavity 110 and a second section 106 having a second cavity 112. Each of the first section 104 and the second section 106 extends from the proximal end portion towards the distal end portion. The first section 104 is adjacent to the second section 106.

The tube 102 includes a rod 114 extending within the first cavity 110 and a plurality of carriers 126 extending within the second cavity 112. The rod 114 can include shape a memory material (e.g., nitinol). Although the carriers 126 are illustrated as a plurality of needle caps 126 note that the carriers 126 can be embodied in other ways (e.g., sleeves), as disclosed herein. The device 100 further includes a plurality of threads 120 (e.g., sutures) extending from the carriers 126. As such, each of the carriers 126 is movable from the second section 106 to the first section 104 when each of the carriers 126 is positioned at the proximal end portion such that the rod 114 (a) engages that respective carrier 126 from which that respective thread extends 120, (b) enters an object 132 (e.g., mammalian tissue) from the proximal end portion of the first cavity 102 at a first point while carrying that respective carrier 126 from which that respective thread extends, and (c) exits the object 132 at a second point while carrying that respective carrier 126 from which that respective thread 120 extends. As shown in FIG. 3, the first point is spaced apart from the second point and the rod 114 arcuately travels between the first point and the second point within the object 132 and each of the carriers 126 is separated from the rod 114 after exiting the object 132. Note that the object 132 can be an inanimate object (e.g. good, garment, shoe, package), an animate object (e.g., mammalian tissue, human tissue, organ tissue, bone tissue, heart tissue, heart valve tissue, bicuspid valve tissue, tricuspid valve tissue), or any other object that can be penetrated, as disclosed herein.

As shown in FIGS. 1-3, the tube 102 is a single tube 102 having a wall 108 partitioning between the first cavity 110 and the second cavity 112, where the wall 108 extends between the rod 114 while the rod 114 extends within the first cavity 110 and at least one of the carriers 126 while that respective carrier 126 extends within the second cavity 112. The tube 102 has a slit 122 extending over the second section 106, where at least one of the threads 120 extends from at least one of the carriers 126 out through the slit 122. The slit 122 extends from the second section 106 to the first section 104 such that the at least one of the threads 120 correspondingly travels from the second section 106 to the first section 104 when at least one of the carriers 126 is moved from the second section 106 to the first section 104. However, note that this configuration can vary. For example, the tube 102 can be formed by a first sub-tube containing the first section 104 and a second sub-tube containing the second section 106, where the first sub-tube and the second sub-tube are adjoined together (e.g., unitary, assembly, fastening, adhering mating, magnetizing) such that the tube 102 is formed.

The device 100 includes the carriers 126 sequentially positioned within the second cavity 112. As such, a topmost carrier 126 is distal from a lowermost carrier 126 within the second cavity 112. As such, in order to cause the lowermost carrier 126 to move from the second section 106 to the first section 104, there is a base 118 (e.g., pusher rod) that has a surface (e.g., outer) that pushes (e.g., plunging action) the topmost carrier 126 within the second section 106 such that the topmost carrier 126 urges the lowermost carrier 126 to move from the second section 106 to the first section 104, as illustrated in FIG. 2. This can be done indirectly, as shown in FIG. 2, or directly when the lowermost carrier 126 and the topmost carrier 126 are sole carriers 126 within the second section 106.

The rod 114 moves within the first section 104 along a first plane (e.g., a vertical plane) and the carriers 126 move within the second section 106 along a second plane (e.g., a vertical plane), where the first plane and the second plane are parallel to each other, although the first plane and the second plane can be not parallel to each other. Accordingly, as illustrated in FIGS. 1-3, the carriers 126 are embodied as a plurality of needle caps 126 each of which mounts onto the rod 114. This can be done in various ways. As illustrated in FIGS. 1-3, the needle caps 126 sequentially mount onto the rod 114 through mating. For example, each of the needle caps 126 can have a female interface and the rod 114 can have a male interface or vice versa, where the female interface receives the male interface when each of the needle caps 126 is mounted onto the rod 114. For example, the rod 114 has a leading portion having a peg 116 forming a male interface and each of the carriers 126 can have an end portion forming a female interface (e.g., dimple). Therefore, the needle caps 126 can sequentially mount onto the rod 114 through mating when the female interface receives the male interface based on the peg 116 engages each of the carriers 126 (e.g., insertion).

Before each of the carriers 126 is mounted onto the rod 114, each of the carriers 126 rests within the first section 104. In order to ensure that each of the carriers within the first section 104 does not unintentionally fall out or otherwise output from the first section 104, the tube 102 has the proximal portion having a lip 124 that retains each of the carriers 126 before the rod 114 mounts that respective carrier 126 and enters the object from the first cavity 104 at the first point. However, note that this configuration can vary where the lip 124 is absent and the rod 114 is timed to sequentially mount each of the carriers 126 as those carriers 126 move from the second section 106 to the first section 104.

As illustrated in FIGS. 1-3, the carriers 126 avoid mounting onto each other within the second section 106. This is so due to the carriers 126 have a longitudinally non-rectilinear structure. In particular, each of the carriers 126 has a leading edge 128 and a tail end 130 between which a non-rectilinear imaginary line can be formed. Although FIGS. 1-3 allow this non-rectilinear imaginary line to be arcuate, other shapes are possible (e.g., sinusoidal, zigzag).

FIG. 4 illustrates an embodiment of a threading device having a tube for sequentially receiving a plurality of carriers according to this disclosure. In particular, a tube 138 (e.g., docking conveyor tube) includes a plurality of arms 146 that receive each of the carriers 126 after each of the carriers 126 exits the object 132 at the second point. Each of the arms 146 includes an edge 140 (e.g., tooth) preventing a backward movement of each of the carriers 126 toward the object 132 when the edge 140 engages (e.g., contacts) each of the carriers 126. The arms 146 cantileveredly extend from the tube 138 and are unitary with the tube 130 although this can vary (e.g., assembly, mating, fastening, adhering, magnetizing). The arms 146 are flush with the tube 138, although non-flush configuration is possible for at least one of the arms 146.

The tube 138 a third cavity through which the carriers 126 sequentially travel upon receipt. In order to ensure that the carriers 126 do not move toward the object 132 within the third cavity, the tube 138 is equipped with a flap 144 that resiliently or elastically extending into the third cavity such that the flap 144 prevents a backward movement of each of the carriers 126 toward the object 132 when each of the carriers 126 passes the flap 144 within the third cavity. Note that the flap 144 is inwardly bent for unidirectional movement of the carriers 126 away from the object 132. As shown in FIG. 4, the tube 138 has an open shape. For example, the open shape is a C-shape but this can vary (e.g., U-shape, V-shape).

Figure 5:
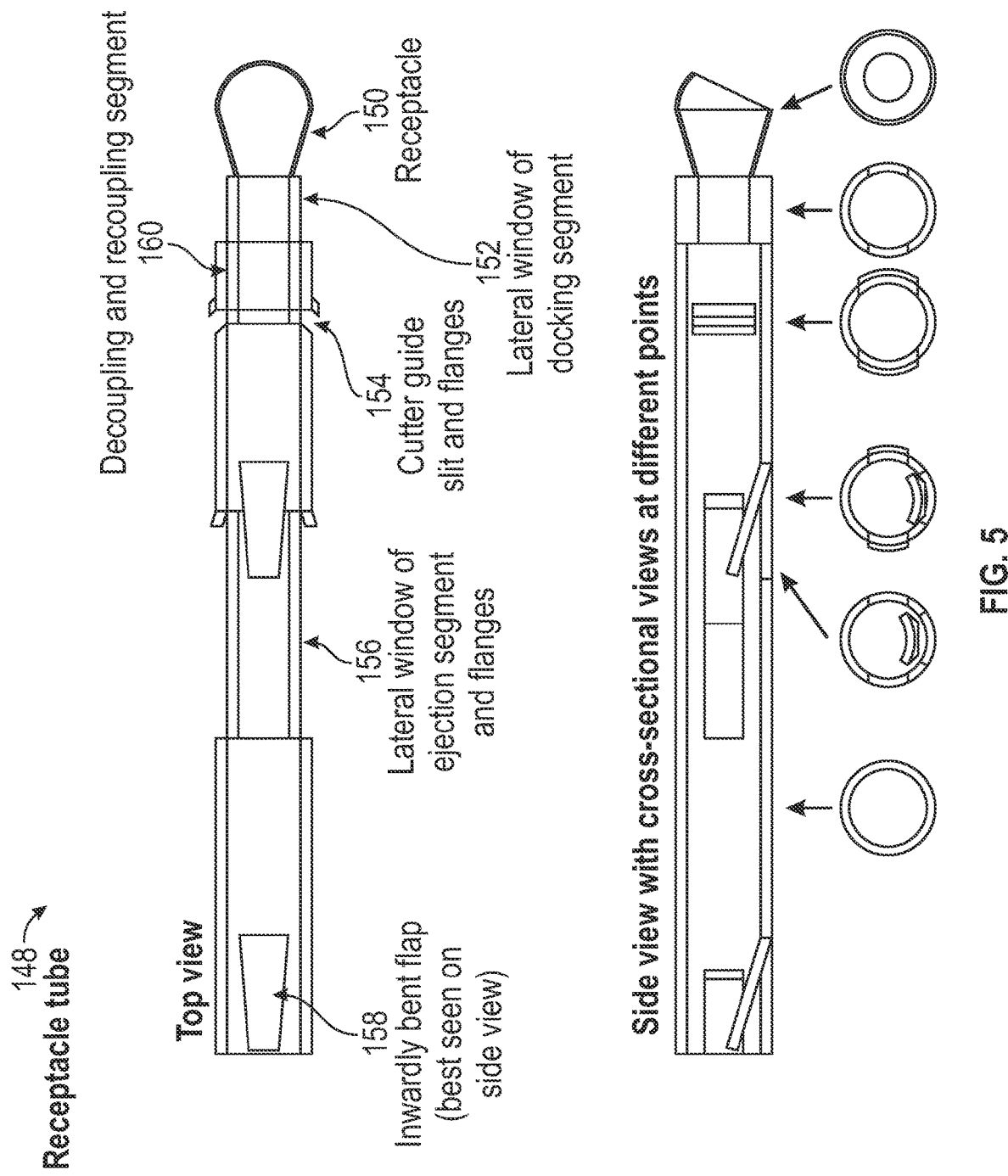
FIG. 5 illustrates an embodiment of a threading device having a tube for sequentially receiving a plurality of carriers according to this disclosure.

FIG. 5 illustrates an embodiment of a threading device having a tube for sequentially receiving a plurality of carriers according to this disclosure. In particular, a tube 148 (e.g., receptacle tube) includes a receptacle 150 (e.g., funnel), a lateral window 152, a cutter guide 154, a lateral window 156, a plurality of flaps 158, and a decoupling and recoupling segment 160. The tube 148 includes a fourth cavity and in order to ensure that the carriers 126 do not move toward the object 132 within the fourth cavity, the tube 148 is equipped with the flaps 158 that resiliently or elastically extending into the fourth cavity such that the flaps 158 prevent a backward movement of each of the carriers 126 toward the object 132 when each of the carriers 126 respectively passes the flaps 158 within the fourth cavity. Note that the flaps 158 are inwardly bent for unidirectional movement of the carriers 126 away from the object 132.

Figure 6:
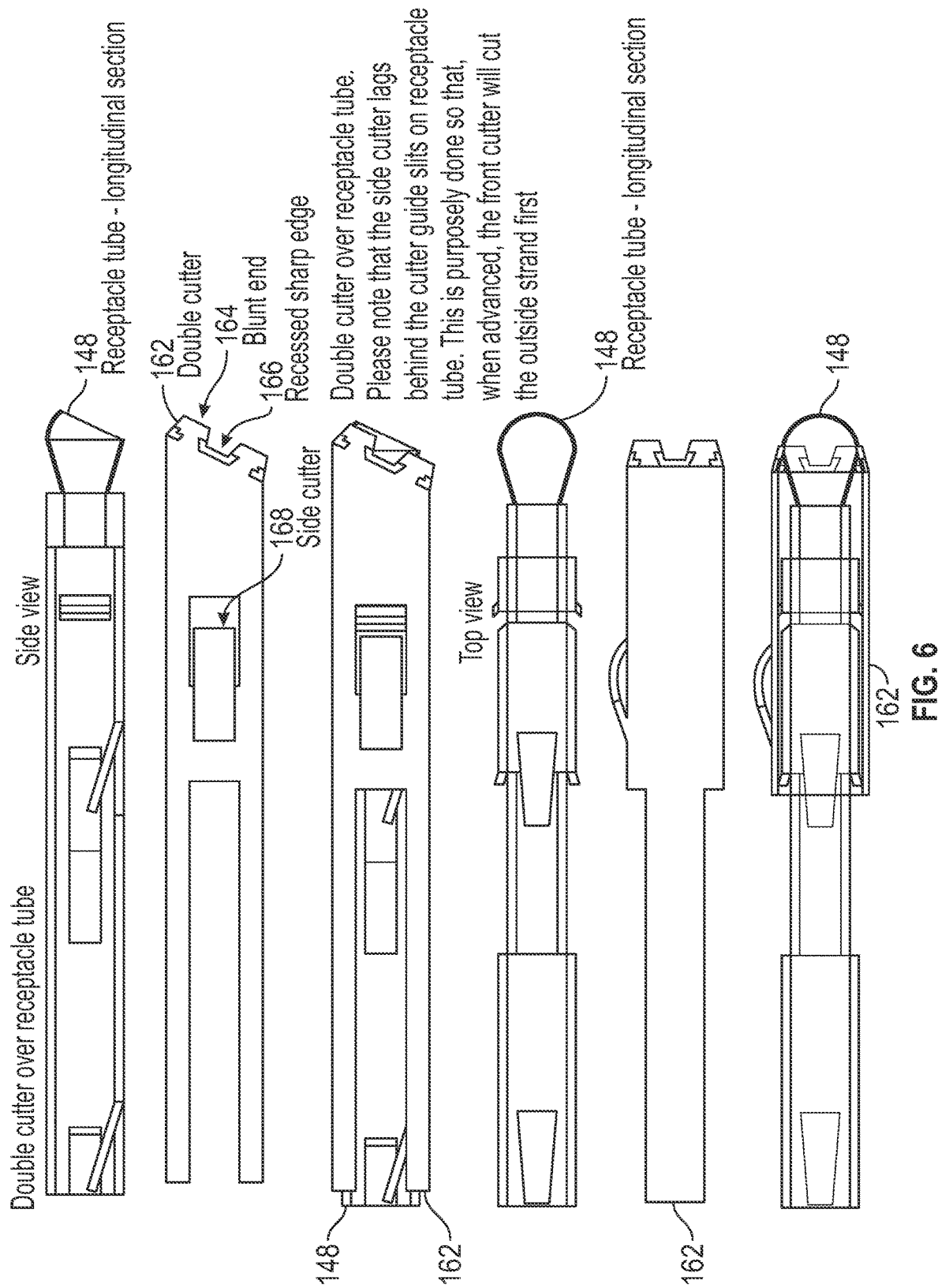
FIG. 6 illustrates an embodiment of a threading device having a plurality of tubes that are concentrically nested for sequentially receiving a plurality of carriers according to this disclosure.

FIG. 6 illustrates an embodiment of a threading device having a plurality of tubes that are concentrically nested for sequentially receiving a plurality of carriers according to this disclosure. In particular, the tube 148 is concentrically nested (e.g., enclosed) within a fifth tube 162 (e.g., double cutter). The fifth tube 162 has a blunt edge 164, a recessed sharp edge 166, and a side cutter 168 (e.g., blade). Note that the side cutter 168 lags behind the cutter guide 154 on the tube 148 in order for the threads 120 that are outside to be cut first. As such, the recessed sharp edge 166 or the side cutter 168 can cut each of the threads 120 extending from each of the carriers 120 upon passing thereof past the recessed sharp edge 166 or the side cutter 168. The side cutter 168 can resiliently or elastically cuts each of the threads 120 extending from each of the carriers 126 upon passing thereof past the side cutter 168.

Figure 7:
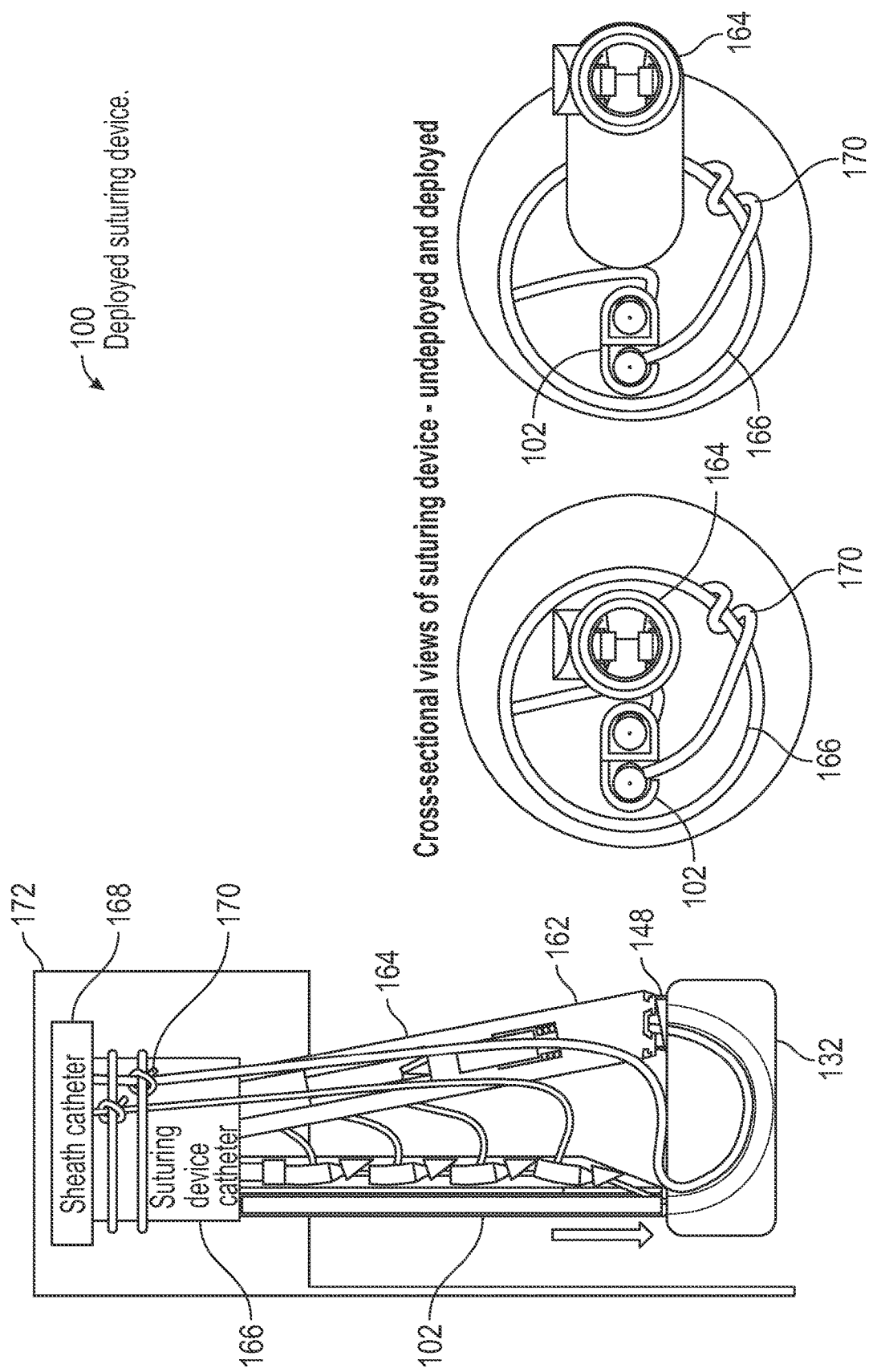
FIG. 7 illustrates an embodiment of a threading device sequentially sending a plurality of carriers into an object and sequentially receiving the carriers from the object according to this disclosure.
Figure 8:
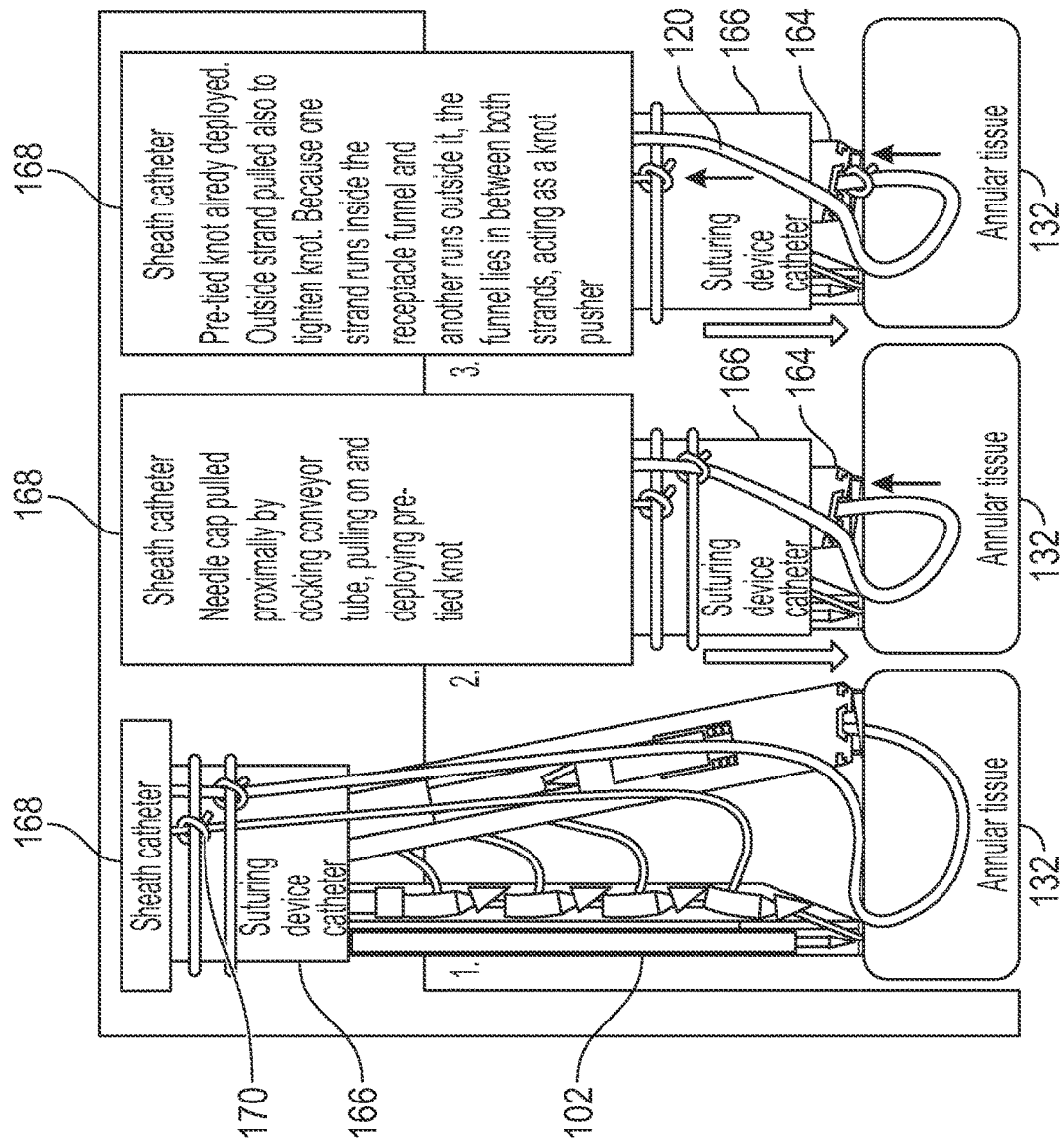
FIG. 8 illustrates an embodiment of a threading device sequentially sending a plurality of carriers into an object and out of the object such that a pre-tied knot is deployed according to this disclosure.

FIG. 7 illustrates an embodiment of a threading device sequentially sending a plurality of carriers into an object and sequentially receiving the carriers from the object according to this disclosure. FIG. 8 illustrates an embodiment of a threading device sequentially sending a plurality of carriers into an object and out of the object such that a pre-tied knot is deployed according to this disclosure. FIG. 13 illustrates an embodiment of a threading device having a tube that outputs a plurality of carriers along an arcuate path and a tube that receives the carriers from the arcuate path according to this disclosure. In particular, the device 100 includes the tube 102 and a tube 164, which contains the tube 148 and the tube 162. The tube 102 and the tube 164 extend from within a tube 166 (e.g., a catheter), which itself extend from within a tube 168 (e.g., sheath catheter 168), which itself extend from within a tube 172 (e.g., an outermost catheter). Any of the tube 102, 164, 148, 162, 166, 168, or 172 can be rigid or flexible, solid or perforated, cross-sectionally symmetrical or asymmetrical or circular or oval or polygonal or teardrop shape. As illustrated in FIG. 7, the tube 102 or the tube 164 can telescope within the tube 166. The tube 166 can telescope within the tube 168. The tube 168 can telescope within the tube 172.

The tube 102 and the tube 164 are not parallel to each other upon extension out of the tube 166, although perpendicular extension is possible. Further, the tube 102 and the object 132 are perpendicular to each other when the rod 114 (a) arcuately travels between the first point within the object 132 (e.g., a point of entry into the object 132) and the second point (e.g., a point of exit from the object 132), (b) enters the object 132 from the first section 104 at the first point (e.g., a point of entry into the object 132) while carrying that respective carrier 126 from which that respective thread 120 extends, or (c) exits the object 132 at the second point (e.g., a point of exit from the object 132) while carrying that respective carrier 126 from which that respective thread 120 extends. However, the tube 102 and the object 132 can be non-perpendicular to each other when the rod 114 (a) arcuately travels between the first point within the object 132 (e.g., a point of entry into the object 132) and the second point (e.g., a point of exit from the object 132), (b) enters the object 132 from the first section 104 at the first point (e.g., a point of entry into the object 132) while carrying that respective carrier 126 from which that respective thread 120 extends, or (c) exits the object 132 at the second point (e.g., a point of exit from the object 132) while carrying that respective carrier 126 from which that respective thread 120 extends. Also, the tube 164 and the object 132 are not perpendicular to each other when the rod 114 (a) arcuately travels between the first point within the object 132 (e.g., a point of entry into the object 132) and the second point (e.g., a point of exit from the object 132), (b) enters the object 132 from the first section 104 at the first point (e.g., a point of entry into the object 132) while carrying that respective carrier 126 from which that respective thread 120 extends, or (c) exits the object 132 at the second point (e.g., a point of exit from the object 132) while carrying that respective carrier 126 from which that respective thread 120 extends. However, the tube 164 and the object 132 can be perpendicular to each other when the rod 114 (a) arcuately travels between the first point within the object 132 (e.g., a point of entry into the object 132) and the second point (e.g., a point of exit from the object 132), (b) enters the object 132 from the first section 104 at the first point (e.g., a point of entry into the object 132) while carrying that respective carrier 126 from which that respective thread 120 extends, or (c) exits the object 132 at the second point (e.g., a point of exit from the object 132) while carrying that respective carrier 126 from which that respective thread 120 extends.

The tube 166 has a plurality of pre-tied knots 170 extending thereover. For example, the threads 120 can extend from the carriers 126 to the pre-tied knot 170 positioned such that the threads 120 extend between the object 132 and the pre-tied knots 170. The pre-tied knots 170 can extend within the tube 168. The pre-tied knots 170 can extend about the tube 166 over the tube 102 such that the threads 120 span between the carriers 126 and the pre-tied knots 170. The pre-tied knots 170 can extend about the tube 166 over the tube 164 such that the threads 120 span between the carriers 126 and the pre-tied knots 170.

As shown in FIGS. 7-8, the tube 164 sequentially receives each of the carriers 126 after each of the carriers 126 exits the object 132 at the second point. The tube 102 or the tube 164 do not pierce or puncture the object 132 (e.g., like a leg standing on a surface), although this is possible (e.g., equipped with a blade or a needle). The tube 106 and the tube 164 are not parallel to each other outside the object 132, although the tube 102 and the tube 164 can be parallel to each other outside the object 132. When threading (e.g., suturing) the carriers 126 can be pulled proximally by the tube 148, which can pull and deploy the pre-tied knots 170 to slide off the tube 166.

Figure 9:
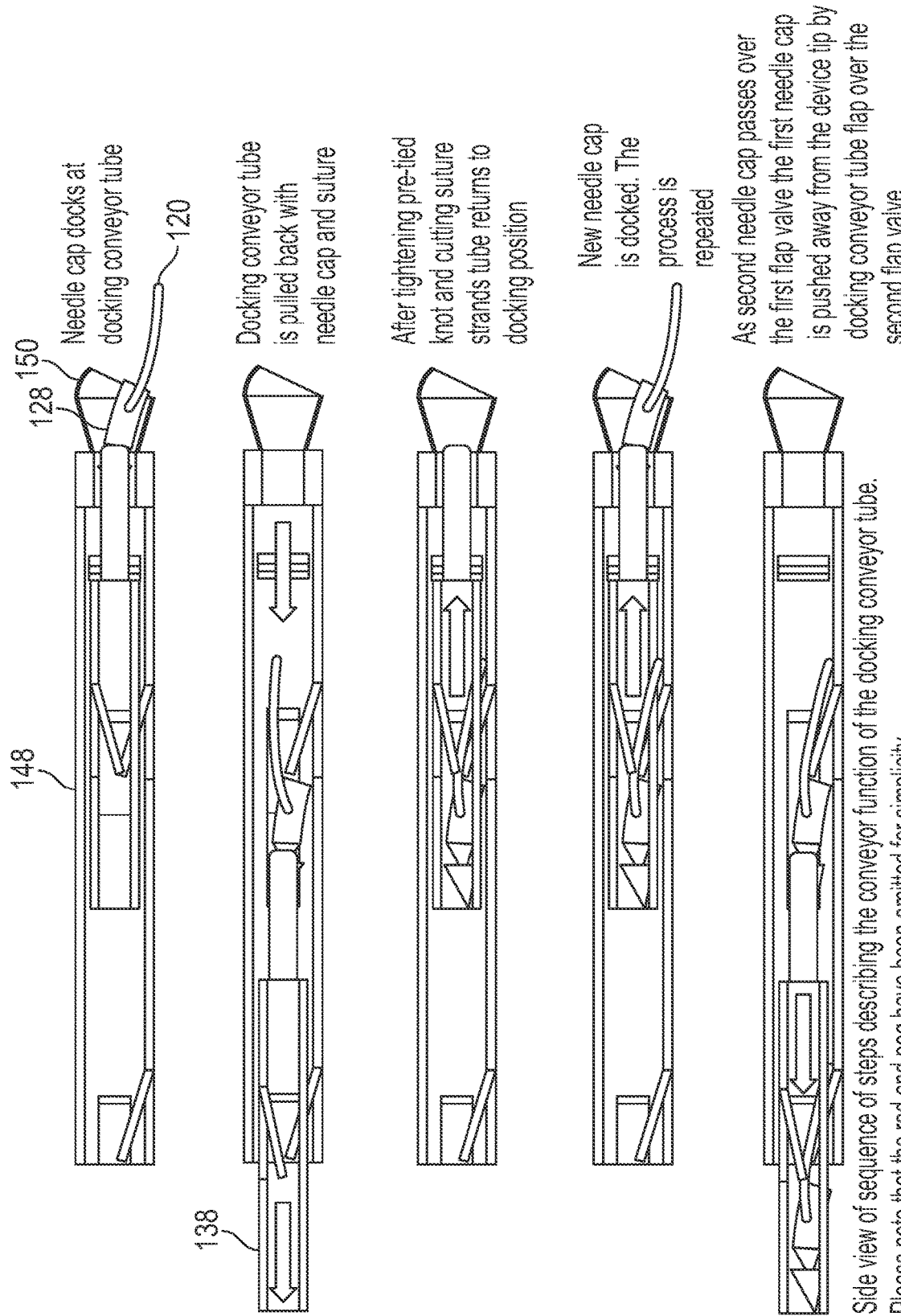
FIG. 9 illustrates an embodiment of a threading device sequentially handling a plurality of carriers according to this disclosure.
Figure 11:
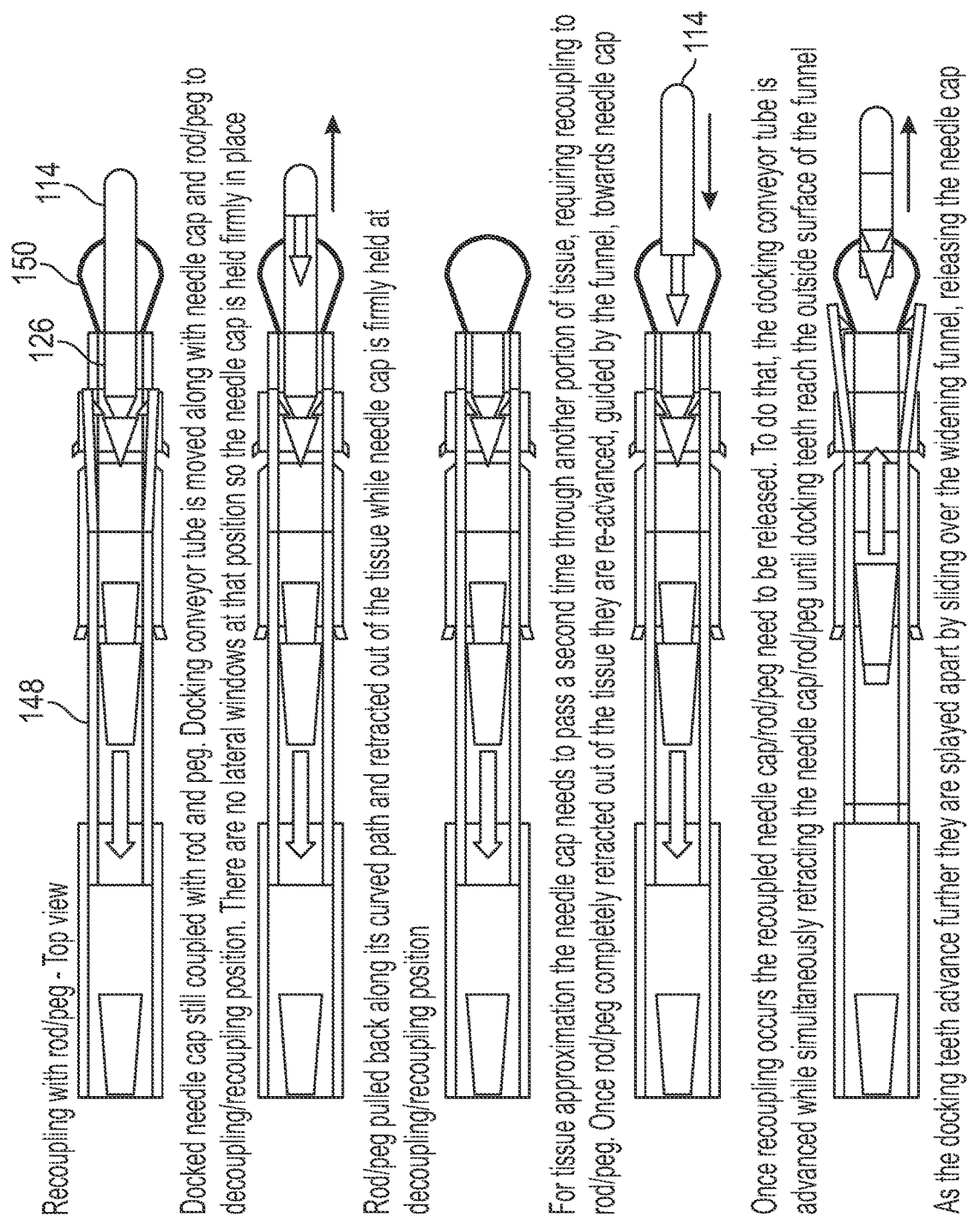
FIG. 11 illustrates an embodiment of a threading device sequentially handling a plurality of carriers after the carriers are sequentially delivered by a rod according to this disclosure.
Figure 12:
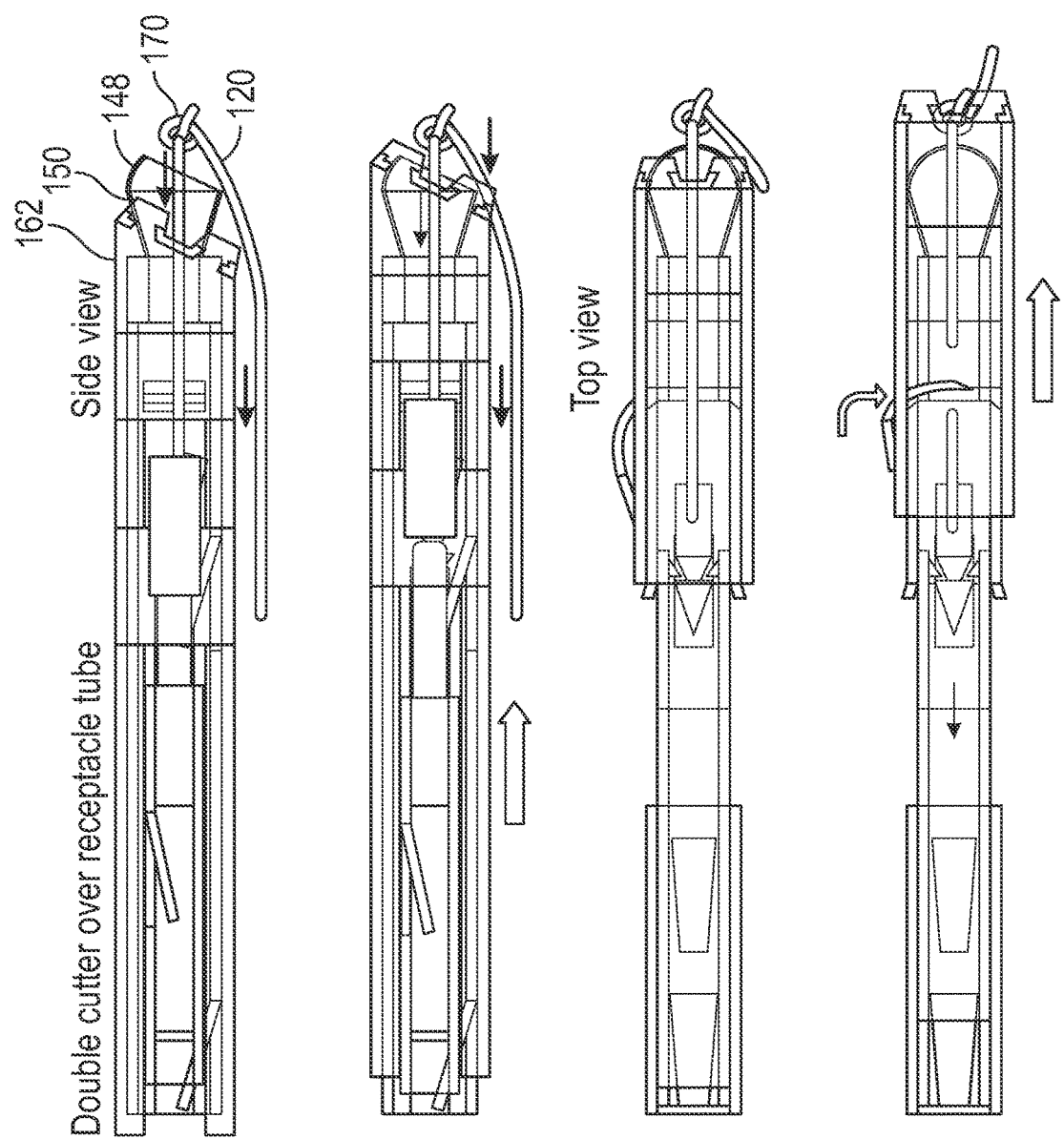
FIG. 12 illustrates an embodiment of a threading device having a tubes hosting a blade that cuts a thread extending from a carrier according to this disclosure.

FIG. 9 illustrates an embodiment of a threading device sequentially handling a plurality of carriers according to this disclosure. FIG. 10 illustrates an embodiment of a threading device sequentially receiving a plurality of carriers from a rod according to this disclosure. FIG. 11 illustrates an embodiment of a threading device sequentially handling a plurality of carriers after the carriers are sequentially delivered by a rod according to this disclosure. FIG. 12 illustrates an embodiment of a threading device having tubes hosting a blade that cuts a thread extending from a carrier according to this disclosure. In particular, each of the carriers 126 docks at the receptacle 150 and the tube 138 is pulled back with each of the carriers 126 and each of the threads 120. After tightening each of the pre-tied knots 170 and cutting various remaining threads 120 strands (e.g., external), the tube 138 returns to its docking position. Then, when a following carrier 126 is docked, this process is repeated. For example, when the following carrier 126 is passes over the one of the flaps 158, a previous carrier 126 (e.g., ahead of the following carrier 126 within the tube 148) is pushed away from the object 132 by one of the flaps 158. The tube 138 can be pulled back along with a decoupled carrier 126 until a corresponding pre-tied knot 170 is deployed and tightened. When a corresponding thread 120 is cut, then that respective carrier 126 is pulled further until passing one of the flaps 158. When the tube 138 is pushed forward against the carrier 126 being held in place by one of the flaps 158, then the arms 146 splay out into lateral windows as slanted surface of the edges 140 slide past the carrier 126 and back into the receptacle 150 guided by lateral extensions. Newly coupled carrier 126 is then docked in place and this process is repeated. Note that the carrier 126 is automatically pushed further back by the flap 144. Resultantly, the carrier 126 moves between the flaps 144, 158.

Note that when the rod 114 sequentially delivers each of the carriers 126, the arms 146 grasp and hold each of the carriers 126 and the rod 114 is retracted back from the second point to the first point along the arcuate path. In some situations, for example, when tissue (or other form of object 132) approximation is desired, some of the carriers may need to pass a second time through another portion of the object 132. This may involve recoupling some of the carriers 126 to the rod 114. For example, once the rod 114 is completely retracted out of the object 132, the rod 114 can be re-advanced and guided by the receptacle 150, back to that respective carrier 126. Once recoupling occurs, the carrier 126, as recoupled, may need to be released. To do that, the tube 138 is advanced while simultaneously retracting the carrier 126 and the rod 114 until the edges 140 reach the receptacle 150 externally. As the edges 140 advance further, the arms 146 are splayed apart by sliding over the receptacle 150, thereby releasing that respective carrier 126. Note that FIG. 12 illustrates the receptacle 150 extending from the tube 148 and each of the pre-tied knots 170 extending from the threads 120. Each of the threads 120 extends through the receptacle 150 into the tube 148 while also extending outside the tube 148 such that the receptacle 150 pushes on each of the pre-tied knots 120. The tube 162 has two cutting edges, as disclosed herein, that can sever each of the threads 120, as disclosed herein. For example, a first cutting edge by the receptacle 150 can cut based on a pulling action exerted on a respective thread 120 and a second cutting edge past the first cutting edge can resiliently or elastically cut the respective thread 120 within the tube 162.

FIG. 14 illustrates an embodiment of a threading device containing a plurality of carriers according to this disclosure. In particular, the rod 114 has a bend 174 that is configured to avoid rotation out of plane within the tube 102. For example, the rod 114 has a leading portion and an end portion, where the rod 114 has the bend 174 between the leading portion and the end portion. Note other techniques for avoiding rotation out of plane within the tube 102 can be employed. For example, the rod 114 can be cross-sectionally not circular (e.g., oval, teardrop, polygonal) or have a cross-section that has a corner (e.g., teardrop, polygonal, triangular).

Note that each of the carriers 126 has the leading edge 128 and the tail end 130 between which the non-rectilinear imaginary line can be formed. Although FIG. 14 allows this non-rectilinear imaginary line to be arcuate, other shapes are possible (e.g., sinusoidal, zigzag). Further, the carrier 126 is shown to have a dimpled end portion (e.g., a female interface) into which the rod 114 is inserted in order for the carrier 126 to be mounted onto the rod 114 (e.g., mating).

FIG. 15 illustrates an embodiment of a rod engaging a carrier with a thread where the thread follows the rod according to this disclosure. FIG. 16 illustrates an embodiment of a rod engaging a carrier with a thread where the thread does not follow the rod according to this disclosure. FIG. 17 illustrates an embodiment of a threading device hosting a rod with a bend according to this disclosure. FIG. 18 illustrates an embodiment of a threading device sequentially hosting a plurality of carriers according to this disclosure. In particular, FIGS. 1-14 depict each of the carriers 126 as a needle cap. However, as shown in FIGS. 15-18, each of the carriers 126 can also be embodied as a mounting interface 176 formed by a sleeve 178 and a thread 180 extending from the sleeve 178. The sleeve 178 can be secured to the thread 180 (e.g., unitary, assembly, fastening, adhering, mating, magnetizing). The sleeve 178 can have a closed shape (e.g., D-shape, O-shape) or an open-shape, which can be C-shaped, although other open shaping is possible (e.g., U-shape, V-shape).

The rod 114 has the bend 174 that is configured to avoid rotation out of plane within the tube 102. For example, the rod 114 has a leading portion and an end portion, where the rod 114 has the bend 174 between the leading portion and the end portion. Note other techniques for avoiding rotation out of plane within the tube 102 can be employed. For example, the rod 114 can be cross-sectionally not circular (e.g., oval, teardrop, polygonal) or have a cross-section that has a corner (e.g., teardrop, polygonal, triangular).

Note that when the carriers 126 is embodied as the mounting interface 176, the rod 114 can includes a tip (e.g., a pointed tip, a tapered tip) that is configured to puncture or pierce the object 132 at the first point and the second point. Also, when the carriers 126 is embodied as the mounting interface 176, the carriers 126 can be stacked on each other within the second section 106 before being moved from the second section 106 to the first section 104. Further, mixing and matching of the carriers 126 is also possible. For example, the tube 102 can have some of the carriers 126 embodied as a needle cap 126 and some of the carriers 126 embodied as a mounting interface 176.

Figure 20:
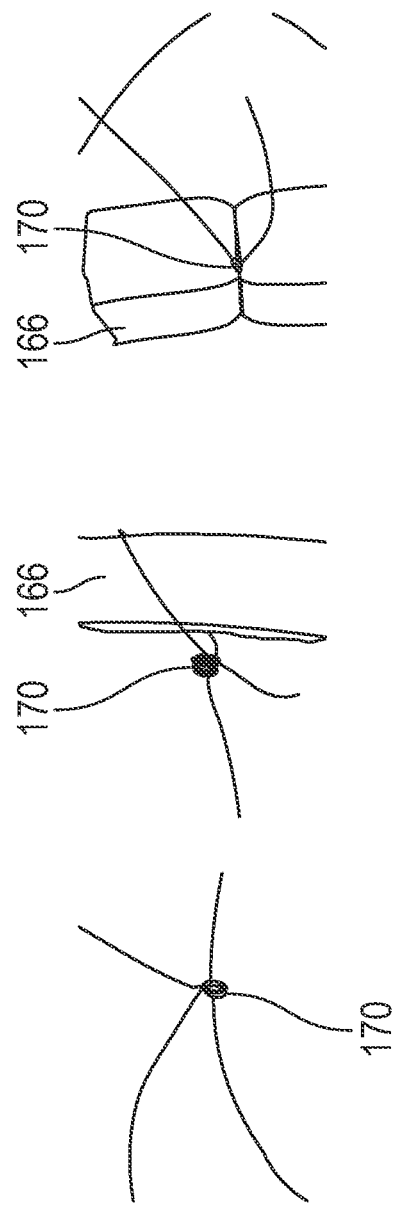
FIG. 20 illustrates an embodiment of a pre-tied knot extending about a flexible tube according to this disclosure.
Figure 21:
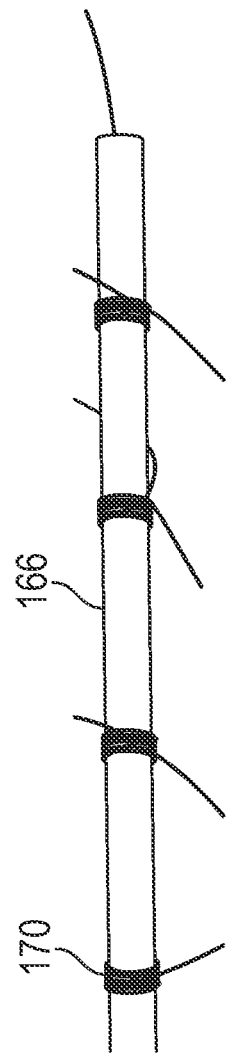
FIG. 21 illustrates an embodiment of a plurality of knots spaced apart from each other while extending about a tube according to this disclosure.

FIG. 19 illustrates an embodiment of a pre-tied knot extending about a rigid tube according to this disclosure. FIG. 20 illustrates an embodiment of a pre-tied knot extending about a flexible tube according to this disclosure. FIG. 21 illustrates an embodiment of a plurality of knots spaced apart from each other while extending about a tube according to this disclosure. In particular, some of the pre-tied knots 170 can be extending about or mounted over the tube 166 while the pre-tied knots 170 are axially spaced apart from each other (e.g., not contacting each other) while extending about or mounted over the tube 166. For example, some of the pre-tied knots 170 can be tied in a Clint knot or a Halyard knot. For example, when each of the pre-tied knots 170 is deployed, the only one knot at a time can be sliding down off the tube 166. Note that the tube 166 can be rigid or flexible or resilient or elastic or deformable.

Figure 24:
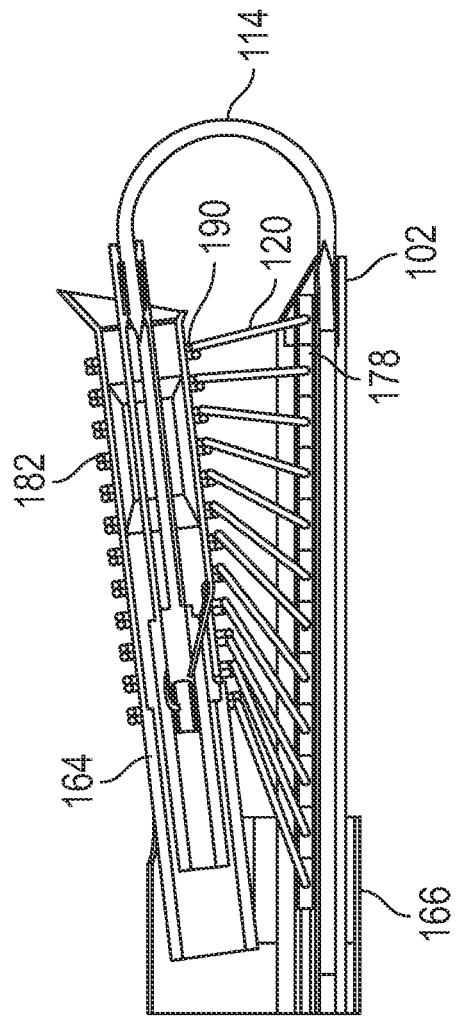
FIG. 24 illustrates an embodiment of a threading device having a first tube sequentially containing a plurality of carriers and a second tube sequentially hosting a plurality of cleats where a plurality of threads span between the carriers and the cleats according to this disclosure.

FIG. 22 illustrates an embodiment of a plurality of knot alternatives according to this disclosure. FIG. 23 illustrates an embodiment of a cleat having a plurality of leaves that resiliently or elastically flex from a default configuration into a non-default configuration while being consecutively offset with each other according to this disclosure. FIG. 24 illustrates an embodiment of a threading device having a first tube sequentially containing a plurality of carriers and a second tube sequentially hosting a plurality of cleats where a plurality of threads span between the carriers and the cleats according to this disclosure. In particular, one of various pre-tied knot 170 alternatives can be embodied a cleat 182 having an outer rim 184 and a plurality of leaves 186 (e.g., sector-shaped) extending from the outer rim 184 toward a common center 188 enclosed by the outer rim 184 at a default position. The leaves 186 elastically or resiliently extend from the rim 184 such that the leaves 186 resiliently or elastically flex from the default position into a non-default position when the tube 164 extends through the rim 184 and the leaves 186 extend over the tube 164. For example, the cleats 182 can be mounted onto the tube 164, where the threads 120 span between the carriers 126 and the cleats 182, whether the carriers are embodied as the needle caps 126 or the mounting interfaces 176, which can be stacked within the second section 106. The cleats 182 can be configured for sterilization.

Each of the cleats 182 has an eyelet 190 extend from the outer rim 184 away from the common center 188. The eyelet 190 is sized to receive a corresponding thread 120. As such, the threads 120 extend into the eyelets 190 before the threads 120 extend through the common centers 188. Note that the cleats 182 can be positioned such that (a) the outer rims 182 are positioned immediately adjacent to each other, (b) the leaves 186 of each of the cleat 182 resiliently or elastically flex from the default position toward or into a next consecutive outer rim 184, and (c) the eyelets 190 are consecutively offset with each other when the tube 164 extends through the outer rims 184. When the cleats 182 extend over or mounted onto the tube 164 the threads 120 span between the carriers 126 and the cleats 182 such that tangling of the threads 120 is avoided.

FIG. 25 illustrates an embodiment of a threading device having a tube with a plurality of fingers for grasping a carrier according to this disclosure. In particular, the tube 164 hosts a plurality of fingers 192 configured to grasp the carriers 126 after each of the carriers 126 exits the object 132 at the second point, whether the carriers are embodied as the needle caps 126 or the mounting interfaces 176. In order to enhance such gripping, the fingers 192 have a plurality of distal end portions having a plurality of edges 194 (e.g., teeth).

FIG. 26 illustrates an embodiment of a threading device scaled relative to a coin according to this disclosure. FIG. 27 illustrates an embodiment of a catheter according to this disclosure.

In some embodiments, the carrier 126 has a lip and the tube 164 has a proximal end section with a rim, where the tube 164 sequentially receives each of the carriers 126 after each of the carriers 126 exits the object 132 at the second point such that the lip abuts the rim on the proximal end section. In some embodiments, the tube 164 can sequentially and frictionally or magnetically or matingly or fastenably receive each of the carriers 126 after each of the carriers 126 exits the object 132 at the second point. For example, each of the carriers 126 can have a first depression or a first projection, and the tube 164 can have a second depression or a second projection, where the tube 164 can sequentially receive each of the carriers 126 after each of the carriers 126 exits the object 132 at the second point based on the first depression engaging the second projection or the first projection engaging the second depression.

In some embodiments, as illustrated in FIGS. 1-27, the threading device 100 is shown for use in a medical setting. The threading device is a trans-catheter suturing device includes a deformable wire (e.g., nitinol or another shape memory material) with a heat-set curve to be inserted as a linear structure and progressively curve back as the deformable wire is advanced through a tissue (e.g., organ tissue, cardiac tissue, lung tissue). The deformable wire can be a solid nitinol (or another shape memory material) rod. Accordingly, the threading device includes a plurality of needle caps an attached suture thread runs inside a tube fitting over an extension (peg) of the deformable rod. The deformable rod is contained within a rigid (or flexible) housing that is designed to accommodate a plurality of needle caps in a parallel tube (e.g., double barrel arrangement). The needle caps are stacked on top of each other and are being progressively moved down by a pusher (e.g., base, platform). As this happens, a bottom needle cap within the parallel tube is guided on an oblique path through an opening between the two barrels, forcing that needle cap into a barrel containing the deformable nitinol rod. The needle caps are hollow at their base to receive the peg extending from the rod in a male/female coupling. This mechanism is similar to a magazine of a gun holding several bullets that are progressively fed into a firing chamber as a preceding bullet is fired. A small retaining lip at a bottom of the barrel containing the deformable nitinol rod holds that needle cap in place (up to a certain force) to resist downward displacement of that needle cap while that needle cap is mated (in any way) with the rod peg. The suture thread is attached at the side of that needle cap base and exits through a vertical (longitudinal) slit that runs an entire length (or less) of the barrel containing the deformable nitinol rod (even through the retaining lip at very bottom). The suture threads run proximally to a pre-tied knot laced around an outer circumference of a suturing device catheter (not sheath catheter although that can be possible as well).

As shown in FIG. 2, there is an engagement of the needle cap (magazine assembly in cross-section) manifested by the needle cap resting in an initial position (A), the rod is pushed down thereby forcing the peg into a base of the needle cap to complete mating (B), and the needle cap is pushed through the retaining lip and out of the magazine assembly ready to suture (C).

As shown in FIG. 3, the needle cap travels through the tissue. The rod coupled with the needle cap is passed through the tissue as the rod is pushed out of its rigid (or flexible) housing and assumes its heat-set curve. Note that the needle cap can also be curved (with same or similar radius of rod curve) as to simulate a constant curvature of a regular needle and to aid in a directional stability of this construct while traversing through the tissue. However, note that the needle cap can be rectilinear. At this point, another main component of the suturing device comes into play, a receiving tube assembly.

As shown in FIGS. 4-12, the receiving tube assembly includes three concentric structures that operably interact among each other to carry out multiple functions beyond just receiving the needle cap. The three structures are a docking conveyor tube (innermost structure), a receptacle tube, and a tubular double cutter, any of which can be rectilinear or non-rectilinear.

The receiving tube assembly is enabled for several functions to be carried out. Some of such functions include receiving the needle cap as the needle cap exits the tissue and guiding the needle to a docking station, which can be performed by a funneled end of the receptacle tube. Some of such functions include docking the needle cap securely in place to allow separation and retraction of the peg and the rod. This can be performed by the docking conveyor tube and can be technically beneficial because such configuration may allow recoupling of peg of the rod and with the needle cap after the rod has been retracted out of the tissue and re-advanced without intervening tissue along a same curved path until recoupling is achieved. At that time, the recoupled needle cap and the rod may be released from the docking station by advancing the docking conveyor tube against a structure that would spread open a set of ratchet teeth hosted via a set of cantilevered arms on the docking station. Because the needle cap and the rod are now recoupled, the needle cap and the rod can be retracted to a position that will allow a second pass of the needle cap and its accompanying suture thread through another edge or portion of tissue, just as with regular suturing. This enables this design to effect approximation of non-contiguous tissue edges, not just single-pass anchoring. Some of such functions include pulling the needle cap into the receiving tube assembly if no second pass is required (or after the second pass is completed). As shown in FIGS. 6-8, because the needle cap is attached to a suture thread that is in turn leading to a pre-tied knot, pulling on the needle cap and thread will deploy and tighten the pre-tied knot (other limb of suture thread runs proximally outside patient for countertraction). Some of such functions include cutting both limbs of the suture thread after knot tightening. This can be performed by a three way (or more or less) tubular cutter, so called because of three cutting surfaces designed to cut the suture strands in a specific sequence, and slits in the receptacle tube. Some of such functions can include disposing used needle cap and suture remnant. This function can be performed by an unidirectional back rake mechanism composed of complimentary simple valve-like cut flaps in the docking conveyor tube and the receptacle tube.

The docking conveyor tube is an innermost of the three concentric structures that constitute the receiving tube assembly. The docking conveyor tube resides inside the receptacle tube and the docking conveyor tube functions to dock the needle cap upon its entry on the receiving tube assembly. The docking conveyor tube does so using a set of docking tooth (e.g., ratchet peg) that falls within a circumferential groove in the needle cap. Once the needle cap is secured by a set of docking teeth extending from a set of docking arms, the deformable nitinol rod and the peg are retracted thereby separating the deformable nitinol rod and the peg from the needle cap. In order for this to happen, at least some clamping force that the docking teeth exert on the needle cap groove can be greater than a force necessary to release the needle cap from the peg. To achieve that, at least some amount of deflection allowed on at least some docking arms is restricted by making a set of lateral windows of a docking segment on the receptacle tube relatively short. As a result, the docking segment of the docking arms that can bend is shorter and becomes stiffer, requiring more force to bend the docking segment enough to release the needle cap. This feature is not only technically beneficial for the docking function but this feature can also apply to recoupling of the needle cap with the peg and the rod. In this instance, the rod and the peg would be pushing against the needle cap, while recoupling so enough force is required to resist at least some push of the rod and exceeds at least some force required for recoupling. As explained herein, at least some teeth on the docking conveyor tube can be pushed against a slanted surface of a receptacle funnel of the receptacle tube to splay those teeth open, releasing the needle cap, as recoupled.

Besides docking the needle cap, another technically beneficial function of the docking conveyor tube is to function as a conveyor for at least some used needle caps and remnant suture thread after each suturing cycle. This is achieved by employing an unidirectional "flap valve" mechanism that is driven by a retrograde motion of the docking conveyor tube inside the receptacle tube. The side view illustration shows the tube with a flap cut on a top portion thereof. This flap is bent inwards into the tube in a structure analogous to a valve leaflet. Notice on the cross-sectional views that the tube does not have a complete circumference (or perimeter if the tube is laterally non-circular). This is done to accommodate a similar flap that has been cut and bent inwards in a bottom portion of the receptacle tube body circumference to function as an opposing leaflet of the "unidirectional valve" structure. These flaps are flexible enough to bend back to allow the needle cap to pass therebetween in a retrograde direction. As the docking conveyor tube is pulled back along with the needle cap that is docked, the needle cap passes over a lower (receptacle tube) flap. At this stage, the docking conveyor tube is pushed forward, splaying the docking teeth with enough force to release the needle cap, slide around the needle cap and return to the docking segment of the receptacle tube. Note that to minimize at least some force required to splay the docking teeth open, at least some lateral windows at an ejection segment of the receptacle tube are longer to allow a partial or full length of the docking arms to bend, becoming less stiff. Small slanted lateral extensions (flanges) at a front end of at least some the lateral windows serve to guide the splayed docking teeth back inside the receptacle tube.

The receptacle tube hosts the receptacle funnel at a distal end of thereof. The receptacle funnel is a component of the receiving tube assembly. Beyond this receptacle function, the receptacle tube also completes a "flap valve" mechanism with the docking conveyor tube, has a set of guide slits for a set of cutter blades and provides a set of lateral windows necessary for needle cap docking, uncoupling and recoupling (used for multiple pass tissue approximation function). Along with the docking conveyor tube, the receptacle tube forms a system for needle cap and suture remnant disposal that is actuated by same movements and steps required for suturing and knot tightening process. Note the receptacle funnel is angled at an end of the receptacle tube. The receptacle tube descends obliquely and this angle allows the receptacle funnel to sit flush with the tissue.

As shown in FIGS. 7-10, the transcatheter suturing device is designed to work with pre-tied preloaded suture knots. This can allow for two suture strands, instead of one, to be cut. The transcatheter suturing device is designed so that the needle cap is docked securely in the receiving tube assembly and pulled back by the docking conveyor tube. This configuration also pulls the suture attached to the needle cap. That strand of the suture leads to the pre-tied knot. As the suture strand attached to the needle cap is pulled, the pre-tied knot is deployed from its resting position around a suturing device catheter. The other strand of the suture lies outside the suturing device catheter and runs proximally outside a patient for tensioning. Because one strand of the suture is being pulled from inside the receptacle tube and the other outside of the receptacle tube, its distal part, the receptacle funnel, lies between the strands and can be used to aid in tensioning the knot. This configuration also places both suture strands in close proximity (because the receptacle funnel would be guided by the suture strand running inside the receptacle funnel to lie on top of the tensioned knot) enabling for a circular tubular cutter (or non-circular or non-tubular) to glide down an outer circumference (or perimeter) of the receptacle tube to cut the outside strand. The distal end of the tubular cutter (or non-tubular) can be slanted to parallel the receptacle funnel, which can be also slanted. The inside strand (attached to the docked needle cap) can be cut relatively last to keep the receptacle tube anchored on the tied knot so that the outside strand remains in close proximity to the receptacle tube and the receptacle funnel for the tubular cutter to cut the outside strand. If the inside strand is cut relatively first or early or before the outside strand, then the knot may be pulled away from the receptacle tube and the cutter by some tension exerted on the knot by the outside strand, thereby complicating (although still possible) and time-consuming to cut the outside strand. To avoid or minimize this use case, a side blade can be incorporated in the tubular cutter so that some sharp recesses at a front end of the cutter reach the outside strand and cut the outside strand first. Further advancement of the tubular cutter will drive the side cutter through a guiding slit in the receptacle tube to its lumen, cutting the tensed inner strand. Damage to tissue or the implant due to advancement of the tubular cutter is avoided or minimized because the sharp surfaces are recessed back. The leading surface of the cutter is blunt (but can be sharp).

As shown in FIGS. 7-8, when the transcatheter suturing device is deployed, the receiving tube assembly is angled slightly so as the receiving tube assembly is deployed and advanced out of the suturing device catheter, which can have a smaller diameter than a bite width of 8 mm (or less or more) needed to achieve a 4 mm (or less or more) bite depth), the receiving tube assembly reaches a spacing for a planned bite width. The pre-tied knots are pre-loaded around the suturing device catheter. Upon pulling of the needle cap inside the receiving tube assembly, the transcatheter suturing device will be pulled into the suturing device catheter. The suture strand can be tensed and will pull down the pre-tied knot, deploying the pre-tied knot from the suturing device catheter.

When the double cutter is positioned over the receptacle tube, the receptacle tube can be with the double cutter in an initial position. The pre-tied knot can be deployed and tension can be held by the inside strand (attached to the needle cap). The pre-tied knot can be tightened by also pulling on the outside strand suture strand and using the receptacle funnel wall as a knot pusher. The outside strand cut relatively first or before the inside strand. The inside strand can then be cut by side cutter afterwards (best seen on top view). As soon as the inside strand is cut, then the remnant is pulled back with the needle cap until the first flap valve is reached and then the needle cap and the suture remnant are held in place by the flap valve, as described herein, while the docking conveyor tube is pushed forward to its initial position for another suture cycle to begin. Matched flap valves are placed in series along the docking conveyor tube and the receptacle tube as to progressively move the used needle caps proximally with each new suture cycle.

As shown in FIGS. 1-12, the threading device allows for tissue anchoring or tissue approximation (multiple passes) and automate as much as possible some, many, most, or all steps involved in a suturing process (even loading and disposal of needles) without needing to remove the threading device for muzzle loading. The threading device cuts significant time by its multi-output capabilities. When the threading device is use for trans-septal procedures, then a septal defect may need to be repaired with an additional device like an occlude or similar, which is additional time and cost spent in that procedure. Because this threading device enables both anchor and tissue approximation, once some, many, most, or all implant anchoring and valve repair procedures are done, then the septal defect may be closed with the threading device when withdrawing the threading device by using its tissue approximation features.

Note that this disclosure may be embodied in many different forms and should not be construed as necessarily being limited to various embodiments disclosed herein. Rather, these embodiments are provided so that this disclosure is thorough and complete, and fully conveys various concepts of this disclosure to one of ordinary skilled in an art to which this disclosure belongs.

Note that various terminology used herein can imply direct or indirect, full or partial, temporary or permanent, action or inaction. For example, when an element is referred to as being "on," "connected," or "coupled" to another element, then the element can be directly on, connected, or coupled to another element or intervening elements can be present, including indirect or direct variants. In contrast, when an element is referred to as being "directly connected" or "directly coupled" to another element, then there are no intervening elements present.

As used herein, various singular forms "a," "an" and "the" are intended to include various plural forms as well, unless specific context clearly indicates otherwise.

As used herein, various presence verbs "comprises," "includes" or "comprising," "including" when used in this specification, specify a presence of stated features, integers, steps, operations, elements, or components, but do not preclude the presence or addition of one or more other features, integers, steps, operations, elements, components, or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "combination", "combinatory," or "combinations thereof" refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. One of ordinary skilled in an art to which this disclosure belongs understands that typically there is no limit on number of items or terms in any combination, unless otherwise apparent from the context.

As used herein, unless otherwise defined, all terms (including technical and scientific terms) used herein have a same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized or overly formal sense unless expressly so defined herein.

As used herein, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements.

Therefore, various example terms "below" and "lower" can encompass both an orientation of above and below.

As used herein, a term "about" or "substantially" refers to a +/−10% variation from a nominal value/term. Such variation is always included in any given value/term provided herein, whether or not such variation is specifically referred thereto.

In particular, a device 100 can be used for an open surgery, a minimally invasive surgery, a laparoscopic surgery, or an end effector robotic surgery. As such, the device 100 can be used for manual surgery or automated surgery. Some examples of surgeries where the device 100 can be employed include laparoscopic surgery, robotic surgery, video-assisted or unassisted thoracoscopic surgery, arthroscopic surgery, natural orifice surgery, endoscopic surgery, gynecologic surgery, cardiac surgery, colorectal surgery, pulmonary surgery, gastric bypass surgery, hysterectomy surgery, dental surgery, urological surgery, brain surgery, or bariatric surgery, or among many others in human (e.g., between newborn until 120 years old, male, female) or animal (e.g., mammal, birds, fish, land animals) applications. However, note that the device 100 can also be applied to non-medical applications, such as Any component described herein can include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

When any component is moved then such move may be driven automatically (e.g., motor, engine, actuator, mechanical linkage, gear mechanism, pulley mechanism, hydraulic mechanism, pneumatic mechanism) or can be driven manually (e.g., user rotation or pulling or pushing or tilting).

A device, as shown in FIGS. 1-27, which can include a suture or a thread, can be packaged, whether alone or with any other devices, whether disclosed herein or not, in a kit. For example, the kit can include a package (e.g., plastic bag, sealed bag, storage container, cardboard box, transport package, consumer package, bubble wrap, foam blanket, garment blanket, can, shrink-wrap, molded pulp, blister pack, plastic box). For example, the package can include a cuboid box, a shipping box, an intermodal container, or others. The package can include one or more devices, as disclosed herein or not disclosed herein. The kit can include a set of instructions on a memory (e.g., mechanical memory, electronic memory, paper page, booklet, laminated card, flash drive, computer disc, website link). The set of instructions can instruct (e.g., text, graphics) a user on how to use a needle driver, as disclosed herein.

Features described with respect to certain embodiments may be combined in or with various some embodiments in any permutational or combinatory manner. Different aspects or elements of example embodiments, as disclosed herein, may be combined in a similar manner.

Although the terms first, second, can be used herein to describe various elements, components, regions, layers, or sections, these elements, components, regions, layers, or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Features described with respect to certain example embodiments can be combined and sub-combined in or with various other example embodiments. Also, different aspects or elements of example embodiments, as disclosed herein, can be combined and sub-combined in a similar manner as well. Further, some example embodiments, whether individually or collectively, can be components of a larger system, wherein other procedures can take precedence over or otherwise modify their application. Additionally, a number of steps can be required before, after, or concurrently with example embodiments, as disclosed herein. Note that any or all methods or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques or tolerances, are to be expected. Thus, various example embodiments of this disclosure should not be construed as necessarily limited to various particular shapes of regions illustrated herein, but are to include deviations in shapes that result, for example, from manufacturing.

Any or all elements, as disclosed herein, can be formed from a same, structurally continuous piece, such as being unitary, or be separately manufactured or connected, such as being an assembly or modules. Any or all elements, as disclosed herein, can be manufactured via any manufacturing processes, whether additive manufacturing, subtractive manufacturing, or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable one of ordinary skilled in an art to which this disclosure belongs to understand this disclosure for various embodiments with various modifications as are suited to a particular use contemplated.

This detailed description has been presented for various purposes of illustration and description, but is not intended to be fully exhaustive or limited to this disclosure in various forms disclosed. Many modifications and variations in techniques and structures will be apparent to one of ordinary skilled in an art to which this disclosure belongs, without departing from a scope and spirit of this disclosure as set forth in various claims that follow. Accordingly, such modifications and variations are contemplated as being included in this disclosure. Scope of this disclosure is defined by various claims, which include known equivalents and unforeseeable equivalents at filing of this disclosure.

What is claimed is:

1. A device comprising:

A first tube having a proximal end portion and a distal end portion, wherein the first tube includes a first section and a second section, wherein each of the first section and the second section extends from the proximal end portion towards the distal end portion, wherein the first section is adjacent to the second section;

a rod extending within the first section;
a plurality of carriers extending within the second section;
a thread extending from each of the carriers, wherein each of the carriers is movable from the second section to the first section when each of the carriers is positioned at the proximal end portion such that the rod (a) engages that respective carrier from which that respective thread extends, (b) enters an object from the proximal end portion of a first cavity at a first point while carrying that respective carrier from which that respective thread extends, and (c) exits the object at a second point while carrying that respective carrier from which that respective thread extends, wherein the first point is spaced apart from the second point, wherein the rod arcuately travels between the first point and the second point, wherein each of the carriers is separated from the rod after exiting the object;
a second tube having a distal end;
wherein the second tube sequentially receives each of the carriers after each of the carriers exits the object at the second point;
wherein the rod is configured to position each of the carriers to be sequentially received into the distal end of the second tube.

2. The device of claim 1, wherein the first tube is a single tube having a wall partitioning between the first section and the second section, wherein the wall extends between the rod and at least one of the carriers.

3. The device of claim 1, wherein the first tube has a slit extending over the second section, wherein at least one of the threads extends from at least one of the carriers out through the slit.

4. The device of claim 3, wherein the slit extends from the second section to the first section such that the at least one of the threads correspondingly travels from the second section to the first section when the at least one of the carriers is moved from the second section to the first section.

5. The device of claim 1, further comprising: a first sub-tube; and a second sub-tube, wherein the first sub-tube and the second sub-tube are adjoined together such that the first tube is formed, wherein the first sub-tube contains the first section, wherein the second sub-tube contains the second section.

6. The device of claim 1, wherein the carriers include a first carrier and a second carrier, wherein the second carrier is distal from the first carrier, and further comprising:
a surface that pushes the second carrier within the second section such that the second carrier urges the first carrier to move from the second section to the first section.

7. The device of claim 1, wherein at least one of the carriers is a needle cap that mounts onto the rod.

8. The device of claim 1, wherein the carriers are a plurality of needle caps that avoid mounting onto each other within the second section.

9. The device of claim 1, wherein at least one the carriers has a leading edge and a tail end between which a non-rectilinear imaginary line is formed.

10. The device of claim 1, wherein the rod includes a shape memory material.

11. The device of claim 1, wherein the rod has a leading portion having a peg forming a male interface, wherein at least one of the carriers has an end portion forming a female interface, wherein the female interface receives the male interface when the peg engages the at least one of the carriers.

12. The device of claim 1, wherein at least one of the threads extends from at least one of the carriers to a pre-tied knot positioned such that the at least one of the threads extends between the object and the pre-tied knot.

13. The device of claim 1, further comprising: a catheter within which the first tube extends.

14. The device of claim 1, wherein the first tube and the object are perpendicular to each other when the rod (a) arcuately travels between the first point and the second point, (b) enters the object from the first section at the first point while carrying that respective carrier from which that respective thread extends, or (c) exits the object at the second point while carrying that respective carrier from which that respective thread extends.

15. The device of claim 1, wherein the first tube and the object are not perpendicular to each other when the rod (a) arcuately travels between the first point and the second point, (b) enters the object from the first section at the first point while carrying that respective carrier from which that respective thread extends, or (c) exits the object at the second point while carrying that respective carrier from which that respective thread extends.

16. The device of claim 1, wherein the first tube has an end portion having a lip that retains at least one of the carriers before the rod enters the object from the first cavity at the first point.

17. The device of claim 1, wherein the object is an animate object.

18. The device of claim 17, wherein the animate object is a heart.

19. The device of claim 18, wherein the animate object is a valve of the heart.

20. The device of claim 1, wherein the rod moves within the first section along a first plane, wherein the carriers move within the second section along a second plane, wherein the first plane and the second plane are parallel to each other.

21. The device of claim 1, wherein the first tube does not pierce or puncture the object.

22. The device of claim 1, further comprising: a catheter within which the first tube and the second tube extend.

23. The device of claim 22, wherein the catheter is a first catheter, and further comprising:
a second catheter within which the first catheter extends.

24. The device of claim 22, further comprising:
a plurality of pre-tied knots extending about the catheter over the first tube such that the threads span between the carriers and the pre-tied knots.

25. The device of claim 24, wherein the pre-tied knots extending about the catheter over the second tube such that the threads span between the carriers and the pre-tied knots.

26. The device of claim 22, further comprising:
a plurality of pre-tied knots extending about the catheter over the second tube such that the threads span between the carriers and the pre-tied knots.

27. The device of claim 1, wherein the rod is configured to avoid rotation out of a plane within the first tube.

28. The device of claim 1, wherein each of the carriers is a sleeve, wherein the rod includes a tip that is configured to puncture the object at the first point and the second point.

29. The device of claim 28, wherein the rod is configured to avoid rotation out of a plane within the first tube.

30. The device of claim 1, wherein the first tube is rigid.

31. The device of claim 1, further comprising: a catheter within which the first tube extends; a plurality of pre-tied knots extending about the catheter over the first tube, wherein the pre-tied knots are spaced apart from each other.

32. The device of claim 1, a plurality of cleats mounted onto the second tube, wherein the threads span between the carriers and the cleats.

33. The device of claim 32, wherein the cleats are configured for sterilization.

* * * * *